US008318697B2

(12) United States Patent
Persing et al.

(10) Patent No.: US 8,318,697 B2
(45) Date of Patent: *Nov. 27, 2012

(54) PROPHYLACTIC AND THERAPEUTIC TREATMENT OF INFECTIOUS AND OTHER DISEASES WITH MONO- AND DISACCHARIDE-BASED COMPOUNDS

(75) Inventors: David H. Persing, Redmond, WA (US); Richard Thomas Crane, Hamilton, MT (US); Gary T. Elliott, Stevensville, MT (US); J. Terry Ulrich, Corvallis, MT (US); Michael J. Lacy, Hamilton, MT (US); David A. Johnson, Hamilton, MT (US); Jory R. Baldridge, Victor, MT (US); Rong Wang, Missoula, MT (US)

(73) Assignee: Corixa Corporation, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/042,312

(22) Filed: Mar. 7, 2011

(65) Prior Publication Data

US 2011/0178034 A1  Jul. 21, 2011

Related U.S. Application Data

(63) Continuation of application No. 11/732,987, filed on Apr. 4, 2007, now Pat. No. 7,902,159, which is a continuation of application No. 10/757,233, filed on Jan. 13, 2004, now abandoned, which is a continuation of application No. 09/991,376, filed on Nov. 20, 2001, now abandoned, which is a continuation-in-part of application No. 09/861,466, filed on May 18, 2001, now Pat. No. 6,800,613.

(60) Provisional application No. 60/281,567, filed on Apr. 4, 2001, provisional application No. 60/205,820, filed on May 19, 2000.

(51) Int. Cl.
*A61K 31/7008* (2006.01)
*A61K 31/7012* (2006.01)

(52) U.S. Cl. .......... 514/62; 514/25; 536/17.9; 536/22.1; 536/55.2

(58) Field of Classification Search .................. None
See application file for complete search history.

(56) References Cited

U.S. PATENT DOCUMENTS

| | | | |
|---|---|---|---|
| 4,436,727 A | 3/1984 | Ribi | |
| 4,844,894 A | 7/1989 | Ribi | |
| 4,866,034 A | 9/1989 | Ribi | |
| 4,877,611 A | 10/1989 | Cantrell | |
| 4,912,094 A | 3/1990 | Myers et al. | |
| 4,987,237 A | 1/1991 | Myers et al. | |
| 5,286,718 A | 2/1994 | Elliott | |
| 5,653,996 A | 8/1997 | Hsu | |
| 5,762,943 A | 6/1998 | Dolovich et al. | |
| 6,013,640 A | 1/2000 | Elliott et al. | |
| 6,113,918 A | 9/2000 | Johnson et al. | |
| 6,303,347 B1 | 10/2001 | Johnson et al. | |
| 6,355,257 B1 | 3/2002 | Johnson et al. | |
| 6,399,590 B2 | 6/2002 | Elliott et al. | |
| 6,525,028 B1 | 2/2003 | Johnson et al. | |
| 6,638,517 B2 | 10/2003 | Reed et al. | |
| 7,541,020 B2 | 6/2009 | Johnson et al. | |
| 2002/0009456 A1 | 1/2002 | Crane | |
| 2002/0032165 A1 | 3/2002 | Johnson et al. | |
| 2002/0048588 A1 | 4/2002 | Johnson et al. | |
| 2003/0139356 A1 | 7/2003 | Persing et al. | |
| 2003/0190333 A1 | 10/2003 | Mossman et al. | |
| 2004/0147480 A1 | 7/2004 | Persing et al. | |
| 2005/0227943 A1 | 10/2005 | Johnson et al. | |

FOREIGN PATENT DOCUMENTS

| | | |
|---|---|---|
| GB | 2 220 211 | 1/1990 |
| WO | WO 97/42947 A | 11/1997 |
| WO | WO 98/50399 A | 11/1998 |
| WO | WO 01/10221 A1 | 2/2001 |
| WO | WO 01/34617 A2 | 5/2001 |
| WO | WO 01/34794 A1 | 5/2001 |
| WO | WO 01/70209 A | 9/2001 |

OTHER PUBLICATIONS

Alderson, Mark R. et al.; "TLR4 agonists as immunomodulatory agents"; 2006, *Endotoxin Research*, vol. 12, pp. 313-319.

Baldridge, Jory et al.; "Immunostimulatory activity of aminoalkyl glucosaminide 4-phosphates (AGPs): induction of protective innate immune responses by RC-524 and RC-529"; 2002, *J. Endotoxin Res.*, vol. 8, pp. 453-458.

Baldridge, Jory et al.; "Monophosphoryl Lipid A and Synthetic Lipid A Mimetics as TLR4-Based Adjuvants and Immunomodulators"; 2003, *Immunological and Clinical Principles*, pp. 235-255.

Baldridge, Jory et al.; "Taking a Toll on human disease: Toll-like receptor 4 agonists as vaccine adjuvants and monotherapeutic agents"; 2004, *Expert Opin. Bio. Ther.*, vol. 4, No. 7, pp. 1129-1138.

Casale, Thomas B. et al.; "Safety of the intranasal toll-like receptor 4 agonist CRX-675 in allergic rhinitis"; 2006, *Ann Allergy Asthma Immunol.*, vol. 97, pp. 454-456.

Chase, J., et al., "Effect of monophosphoryl lipid A on host resistance to bacterial infection," *Infection and Immunity*, vol. 53(3), pp. 711-712 (Sep. 1986).

Check, William; "Innate Immunity Depends on Toll-Like Receptors"; 2004, *ASM News*, vol. 70, No. 7, pp. 317-322.

Cluff, Christopher W. et al.; "Synthetic Toll-Like Receptor 4 Agonists Stimulate Innate Resistance to Infectious Challenge"; 2005, *Infection and Immunity*, vol. 73, No. 5, pp. 3044-3052.

(Continued)

*Primary Examiner* — Leigh Maier

(57) ABSTRACT

Methods and compositions for treating or ameliorating diseases and other conditions, such as infectious diseases, autoimmune diseases and allergies are provided. The methods employ mono- and disaccharide-based compounds for selectively stimulating immune responses in animals and plants.

13 Claims, 26 Drawing Sheets

OTHER PUBLICATIONS

Fang, F.; "Mechanisms of nitric oxide-related antimicrobial activity"; 1999, *J. Clin. Invest.* vol. 99, No. 12, pp. 2818-2825.

Fort, Madeline M. et al.; "A Synthetic TLR4 Antagonist Has Anti-Inflammatory Effects in Two Murine Models of Inflammatory Bowel Disease"; 2005, *The Journal of Immunology*, vol. 174, pp. 6416-6423.

Gustafson, G.L., et al., "Monophosphoryl lipid as a prophylactic for sepsis and septic shock," *Bacterial Endotoxins: Lipopolysaccharides*, vol. 392, pp. 567-579 (1995).

Gustafson and Rhodes, "A Rationale for the Prophylactic Use of Monophosphoryl Lipid A in Sepsis and Septic Shock," *Biochemical and Biophysical Research Communications*, vol. 182, No. 1, pp. 269-275 (1992).

Hovde, Carolyn J. et al.; "APGs (Lipid A mimetics) for protection against pulmonary plague"; 2007, Presentation from the 5th Annual ASM Biodefense and Emerging Infectious Diseases Research Meeting, 34 pages.

Ismaili, Jamila et al.; "Monophosphoryl Lipid A Activates Both Human Dendritic Cells and T Cells"; 2002, *J. Immunology*, vol. 168, pp. 926-932.

Johnson, et al., "3-*O*-desacyl monophosphoryl lipid A derivatives: synthesis and immunostimulant activities," *J. Med. Chem.*, vol. 42, pp. 4640-4649 (1999).

Kirschning, et al., "Human toll-like receptor 2 confers responsiveness to bacterial lipopolysaccharide," *J. Exp. Med.*, vol. 188(11), pp. 2091-2097 (Dec. 7, 1998).

Luxameechanporn, Thongchai et al.; "Evaluation of Importance of Toll-like Receptor 4 in Acute *Streptococcus pneumoniae* Sinusitis in Mice"; 2005, *Arch Otolaryngol Head Neck Surgery*, vol. 131, pp. 1001-1006.

Ogawa, T., et al., "Immunopharmacological activities of the nontoxic monophosphoryl lipid A of *Porphyromonas gingivalis*," *Vaccine* vol. 14(1), pp. 70-76 (1996).

Persing, David H. et al.; "Taking toll: lipid A mimetics as adjuvants and immunomodulators"; 2002, *Trends in Microbiology*, vol. 10, No. 10, pp. S32-S37.

Persing, David H. et al.; "Toll-like receptor 4 agonists as vaccine adjuvants"; 2006, *Immunopotentiators in Modern Vaccines*, pp. 93-107.

Poltorak, et al., "Defective LPS signaling in C3H/HeJ and C57BL/10ScCr mice: mutations in *Tlr4* gene," *Science*, vol. 282, pp. 2085-2088 (Dec. 11, 1998).

Quesniaix et al., "Toll-Like Receptors: emerging targets of immunomodulation", *Exp. Opin. Ther. Pat.* (2004) vol. 14, pp. 85-100.

Qureshi, et al., "Endotoxin-tolerant mice have mutations in toll-like receptor 4(*Tlr4*)," *J. Exp. Med.*, vol. 189(4), pp. 615-625 (Feb. 15, 1999).

Stover, Axel G. et al.; "Structure-Activity Relationship of Synthetic Toll-like Receptor 4 Agonists"; 2004, *The Journal of Biological Chemistry*, vol. 279, No. 6, pp. 4440-4449.

Tiberio, Lorrie et al.; "Host factors impacting the innate response in humans to the candidate adjuvants RC529 and monophosphoryl lipid A"; 2004, *Vaccine*, vol. 22, pp. 1515-1523.

Ulrich, et al., *Vaccine Design: The Subunit and Adjuvant Approach*, Powell and Newman Eds.; Plenum: New York, 495-524 (1995).

Wang, J. et al.; "Macrophages are a significant source of type 1 cytokines during mycobacterial infection"; 1999, *J. Clin. Invest.*, vol. 103, No. 7, pp. 1023-1029.

Yang, et al., "Toll-like receptor-2 mediates lipopolysaccharide-induced cellular signaling," *Nature*, vol. 395, pp. 284-288 (Sep. 17, 1998).

RC-547  RC-554

RC-555  RC-557

RC-558  RC-560

Symptoms Following Influenza Challenge L-Seryl-666 versus L-Seryl-000

Numbers in parenthesis represent percent

Figure 12

PROPHYLACTIC AND THERAPEUTIC TREATMENT OF INFECTIOUS AND OTHER DISEASES WITH MONO- AND DISACCHARIDE-BASED COMPOUNDS

CROSS-REFERENCES TO RELATED APPLICATIONS

This application is a continuation of U.S. patent application Ser. No. 11/732,987, filed Apr. 4, 2007, now issued as U.S. Pat. No. 7,902,159 on Mar. 8, 2011, which is a continuation of U.S. patent application Ser. No. 10/757,233, filed Jan. 13, 2004, now abandoned, which is a continuation of U.S. patent application Ser. No. 09/991,376, filed Nov. 20, 2001, now abandoned, which is a continuation-in-part of U.S. patent application Ser. No. 09/861,466, filed May 18, 2001, now issued as U.S. Pat. No. 6,800,613 on Oct. 5, 2004, which application claims the benefit of U.S. Provisional Patent Application No. 60/281,567, filed Apr. 4, 2001, which application claims the benefit of U.S. Provisional Patent Application No. 60/205,820, filed May 19, 2000, the disclosures of which are incorporated herein by reference in their entirety.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The innate immune system coordinates the inflammatory response to pathogens by a system that discriminates between self and non-self via receptors that identify classes of molecules synthesized exclusively by microbes. These classes are sometimes referred to as pathogen associated molecular patterns (PAMPs) and include, for example, lipopolysaccharide (LPS), peptidoglycans, lipotechoic acids, and bacterial lipoproteins (BLPs).

LPS is an abundant outer cell-wall constituent from gram-negative bacteria that is recognized by the innate immune system. Although the chemical structure of LPS has been known for some time, the molecular basis of recognition of LPS by serum proteins and/or cells has only recently begun to be elucidated. In a series of recent reports, a family of receptors, referred to as Toll-like receptors (TLRs), have been linked to the potent innate immune response to LPS and other microbial components. All members of the TLR family are membrane proteins having a single transmembrane domain. The cytoplasmic domains are approximately 200 amino acids and share similarity with the cytoplasmic domain of the IL-1 receptor. The extracellular domains of the Toll family of proteins are relatively large (about 550-980 amino acids) and may contain multiple ligand-binding sites.

The importance of TLRs in the immune response to LPS has been specifically demonstrated for at least two Toll-like receptors, Tlr2 and Tlr4. For example, transfection studies with embryonic kidney cells revealed that human Tlr2 was sufficient to confer responsiveness to LPS (Yang et al., *Nature* 395:284-288 (1998); Kirschning et al. *J Exp Med.* 11:2091-97 (1998)). A strong response by LPS appeared to require both the LPS-binding protein (LBP) and CD14, which binds LPS with high affinity. Direct binding of LPS to Tlr2 was observed at a relatively low affinity, suggesting that accessory proteins may facilitate binding and/or activation of Tlr2 by LPS in vivo.

The importance of Tlr4 in the immune response to LPS was demonstrated in conjunction with positional cloning in lps mutant mouse strains. Two mutant alleles of the mouse lps gene have been identified, a semidominant allele that arose in the C3H/HeJ strain and a second, recessive allele that is present in the C57BL/10ScN and C57BL/10ScCr strains. Mice that are homozygous for mutant alleles of lps are sensitive to infection by Gram-negative bacteria and are resistant to LPS-induced septic shock. The lps locus from these strains was cloned and it was demonstrated that the mutations altered the mouse Tlr4 gene in both instances (Portorak et al., *Science* 282:2085-2088 (1998); Qureshi et al., *J Exp Med* 4:615-625 (1999)). It was concluded from these reports that Tlr4 was required for a response to LPS.

The biologically active endotoxic sub-structural moiety of LPS is lipid-A, a phosphorylated, multiply fatty-acid-acylated glucosamine disaccharide that serves to anchor the entire structure in the outer membrane of Gram-negative bacteria. We previously reported that the toxic effects of lipid A could be ameliorated by selective chemical modification of lipid A to produce monophosphoryl lipid A compounds (MPL☐ immunostimulant; Corixa Corporation; Seattle, Wash.). Methods of making and using MPL☐ immunostimulant and structurally like compounds in vaccine adjuvant and other applications have been described (see, for example, U.S. Pat. Nos. 4,436,727; 4,877,611; 4,866,034 and 4,912,094; 4,987,237; Johnson et al., *J Med Chem* 42:4640-4649 (1999); Ulrich and Myers, in *Vaccine Design: The Subunit and Adjuvant Approach*; Powell and Newman, Eds.; Plenum: New York, 495-524, 1995; the disclosures of which are incorporated herein by reference in their entireties). In particular, these and other references demonstrated that MPL☐ immunostimulant and related compounds had significant adjuvant activities when used in vaccine formulations with protein and carbohydrate antigens for enhancing humoral and/or cell-mediated immunity to the antigens.

Moreover, we have previously described a class of synthetic mono- and disaccharide mimetics of monophosphoryl lipid A, referred to as aminoalkyl glucosaminide phosphates (AGPs), for example in U.S. Ser. Nos. 08/853,826, now U.S. Pat. No. 6,113,918, Ser. Nos. 09/074,720, 09/439,839, now U.S. Pat. No. 6,303,347, and in PCT/US98/09385 (WO 98/50399, Oct. 12, 1998) the disclosures of which are incorporated herein by reference in their entireties. Like monophosphoryl lipid A, these compounds have been demonstrated to retain significant adjuvant characteristics when formulated with antigens in vaccine compositions and, in addition, have similar or improved toxicity profiles when compared with monophosphoryl lipid A. A significant advantage offered by the AGPs is that they are readily producible on a commercial scale by synthetic means.

Although monophosphoryl lipid A and the AGPs have been described primarily for use in combination with antigens in vaccine formulations, their use as monotherapies, in the absence of antigen, for the prophyhlactic and/or therapeutic treatment of plant and animal diseases and conditions, such as infectious disease, autoimmunity and allergies, has not been previously reported.

The present invention, as a result of a growing understanding of certain mechanisms underlying the activities of monophosphoryl lipid A and AGP compounds, makes possible the novel therapeutic opportunities described herein.

BRIEF SUMMARY OF THE INVENTION

In one aspect, the present invention provides methods for treating, ameliorating or substantially preventing a disease or condition in an animal by administering an effective amount of a compound having the formula:

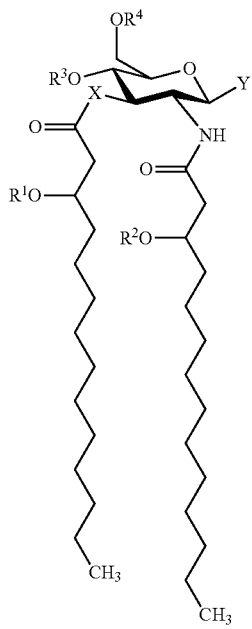

(I)

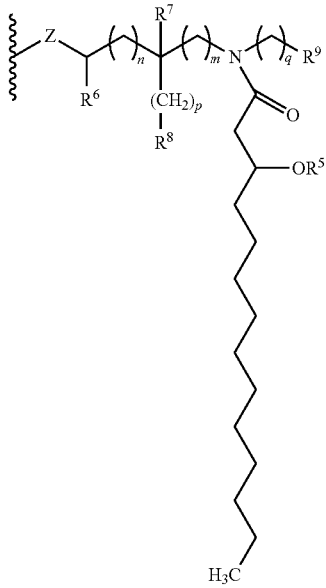

(Ia)

and

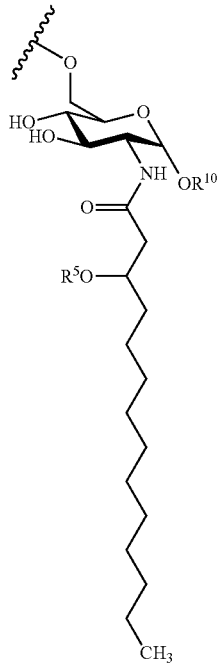

(Ib)

and pharmaceutically acceptable salts thereof, wherein X is —O— or —NH—; $R^1$ and $R^2$ are each independently a ($C_2$-$C_{24}$)acyl group, including saturated, unsaturated and branched acyl groups; $R^3$ is —H or —$PO_3R^{11}R^{12}$, wherein $R^{11}$ and $R^{12}$ are each independently —H or ($C_1$-$C_4$)alkyl; $R^4$ is —H, —$CH_3$ or —$PO_3R^{13}R^{14}$, wherein $R^{13}$ and $R^{14}$ are each independently selected from —H and ($C_1$-$C_4$)alkyl; and Y is a radical selected from the formulae:

wherein the subscripts n, m, p and q are each independently an integer of from 0 to 6; $R^5$ is a ($C_2$-$C_{24}$)acyl group (including, as above, saturated, unsaturated and branched acyl groups); $R^6$ and $R^7$ are independently selected from H and $CH_3$; $R^8$ and $R^9$ are independently selected from H, OH, ($C_1$-$C_4$)alkoxy, —$PO_3H_2$, —$OPO_3H_2$, —$SO_3H$, —$OSO_3H$, —$NR^{15}R^{16}$, —$SR^{15}$, —CN, —$NO_2$, —CHO, —$CO_2R^{15}$, —$CONR^{15}R^{16}$, —$PO_3R^{15}R^{16}$, —$OPO_3R^{15}R^{16}$, —$SO_3R^{15}$ and —$OSO_3R^{15}$, wherein $R^{15}$ and $R^{16}$ are each independently selected from H and ($C_1$-$C_4$)alkyl; $R^{10}$ is selected from H, $CH_3$, —$PO_3H_2$, ω-phosphonooxy($C_2$-$C_{24}$)alkyl, and ω-carboxy($C_1$-$C_{24}$)alkyl; and Z is —O— or —S—; with the proviso that when $R^3$ is —$PO_3R^{11}R^{12}$, $R^4$ is other than —$PO_3R^{13}R^{14}$.

In certain illustrative aspects of the invention, the above methods are employed in treating, ameliorating or substantially preventing infectious diseases, autoimmune diseases and allergies.

The present invention, in other aspects, provides pharmaceutical compositions comprising one or more of the compounds described above in a suitable excipient, formulated and/or administered in the absence of exogenous antigen.

BRIEF DESCRIPTION OF THE DRAWINGS

FIG. 12 is a graph showing clinical symptoms following intranasal administration of L-Seryl 666 versus L-Seryl 000 Aminoalkyl Glucosaminide Phosphates monotherapy and influenza challenge.

DETAILED DESCRIPTION OF THE INVENTION

Illustrative Prophylactic and Therapeutic Applications

Figure 1:
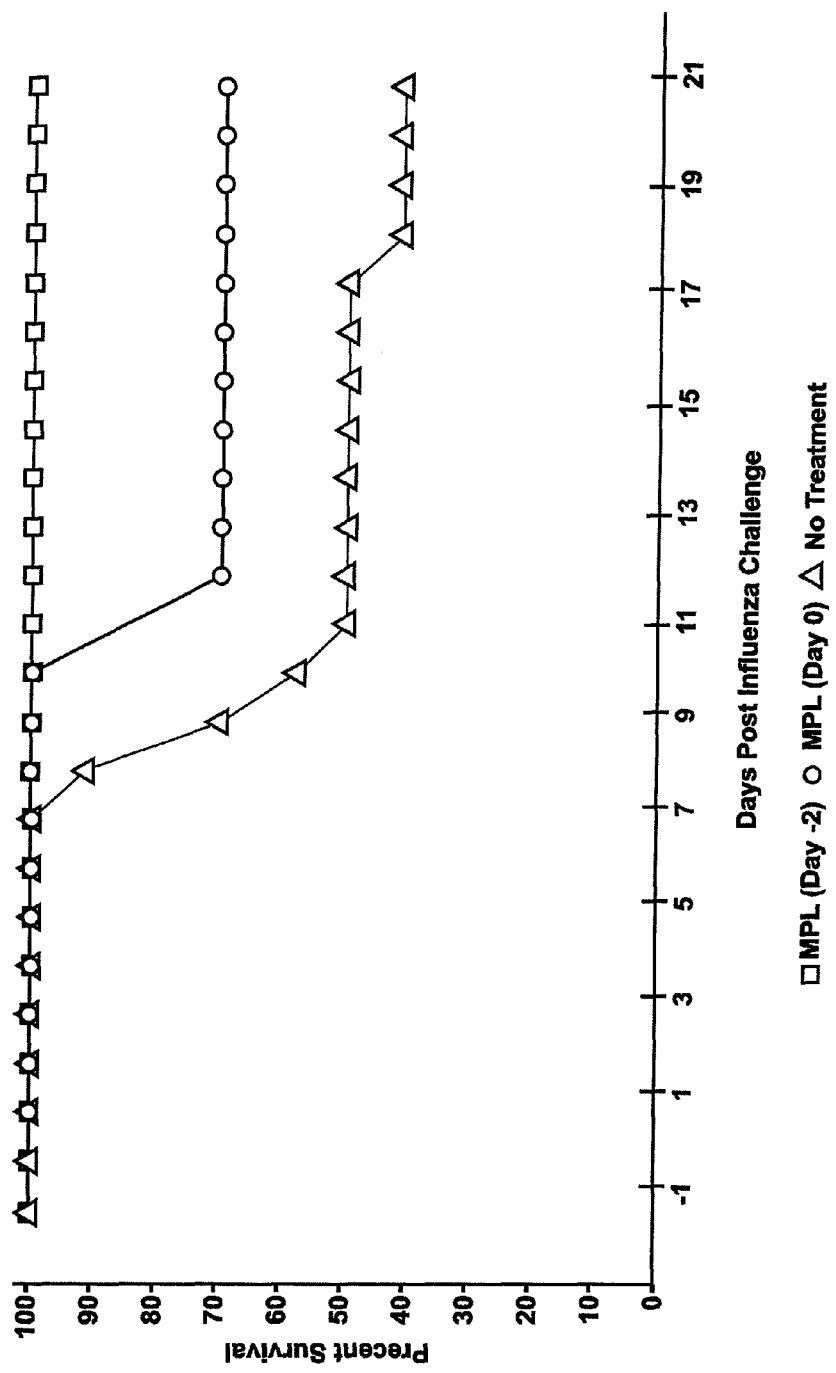
FIG. 1 is a graph depicting the nonspecific protection of mice against lethal influenza challenge following or coincident with MonoPhosphoryl Lipid A (MPL) administration.

The present invention broadly concerns prophylactic and therapeutic methods of treating certain diseases and other medical conditions by administration of an effective amount of one or more mono- or disaccharide compounds described herein or a pharmaceutical composition comprising one or more such compounds. While certain of the mono- and disaccharide compounds have been described for use as adjuvants in combination with exogenously administered antigens in vaccine formulations, and for use in certain other applications, the present invention provides novel therapeutic methods that employ the compounds preferably in monotherapeutic applications, i.e., in the absence of exogenously administered antigen.

Thus, in one aspect, the present invention provides methods for treating, ameliorating and/or substantially preventing infectious diseases in eukaryotic subjects, particularly in animals, preferably in humans. Given the importance of TLR-mediated signalling in the innate immune response to microbial challenge, the ability to stimulate such pathways selectively and with minimal toxicity represents a powerful approach for prophylactic and/or therapeutic treatment modalities against a wide range of infectious agents.

The methods described herein are applicable against essentially any type of infectious agent, including bacteria, viruses, parasites, and fungi. Illustratively, the invention is useful for the prophylactic and/or therapeutic treatment of bacterial infections by species from *Pseudomonas, Escherichia, Klebsiella, Enterobacter, Proteus, Serratia, Candida, Staphylococci, Streptococci, Chlamydia, Mycoplasma* and numerous others. Illustrative viral conditions that may be treated in accordance with the invention include those caused, for example, by Influenza viruses, Adenoviruses, parainfluenza viruses, Rhinoviruses, respiratory syncytial viruses (RSVs), Herpes viruses, Cytomegaloviruses, Hepatitis viruses, e.g., Hepatitis B and C viruses, and others. Illustrative fungi include, for example, *Aspergillis, Candida albicans, Cryptococcus neoformans, Coccidioides immitus*, and others.

In one illustrative embodiment, the invention provides methods for the treatment of subjects, particularly immunocompromised subjects, that have developed or are at risk for developing infections, such as nosocomial bacterial and viral infections. About 2 million of the 40 million individuals hospitalized every year develop nosocomial infection during their stay and about 1% of these, or about 400,000 patients, develop nosocomial pneumonia, more than 7000 of which die. This makes nosocomial pneumonia the leading cause of death in hospital-acquired infections. Thus, this embodiment fills a significant need for effective prophylactic approaches in the treatment of nosocomial infections.

In a related embodiment, the present invention provides prophylactic treatments for immunocompromised patients, such as HIV-positive patients, who have developed or are at risk for developing pneumonia from either an opportunistic infection or from the reactivation of a suppressed or latent infection. In 1992, about 20,000 cases of *Pneumocystis carinii* infections in AIDS patients were reported in the U.S. alone. Additionally, 60-70% of all AIDS patients get *P. carinii* at some time during their illness. Thus, the present invention in this embodiment provides effective prophylactic methods for this at-risk population.

In another related embodiment, the methods of the present invention are used for treating other patient populations that may be immunocompromised and/or at risk for developing infectious diseases, including, for example, patients with cystic fibrosis, chronic obstructive pulmonary disease and other immunocompromized and/or institutionalized patients.

In support of these and other embodiments of the invention, we have demonstrated that pre-challenge administration of an illustrative compound of the present invention in immunocompromised mice provides significant prophylactic protection against infection by *Pneumocystis carinii*. (See Example 1).

In another aspect of the invention, the mono- and disaccharide compounds described herein are employed in methods for treating, ameliorating or substantially preventing allergic disorders and conditions, such as sinusitis, chronic rhinosinusitus, asthma, atopic dermatitis and psoriasis. This approach is based at least in part on the ability of the mono- and disaccharide compounds to activate the production of cytokines from target cells that can compete with stereotypic allergic-type cytokine responses characterized by IL-4 production or hyperresponsiveness to IL-4 activity. Administration of certain of the mono- and disaccharide compounds disclosed herein results in IFN-gamma and IL-12 expression from antigen processing and presenting cells, as well as other cells, resulting in down regulation of cytokines associated with allergic responses such as IL-4, 5, 6, 10 and 13.

In another aspect of the invention, mono- and disaccharide compounds are employed in methods for treating autoimmune diseases and conditions. The mono- and disaccharide compounds for use in this embodiment will typically be selected from those capable of antagonizing, inhibiting or otherwise negatively modulating one or more Toll-like receptors, particularly Tlr2 and/or Tlr4, such that an autoimmune response associated with a given condition is ameliorated or substantially prevented. Illustratively, the methods provided by this embodiment can be used in the treatment of conditions such as inflammatory bowel disease, rheumatoid arthritis, chronic arthritis, multiple sclerosis and psoriasis.

While not wishing to be bound by theory, it is believed that the efficacy of the prophylactic and therapeutic applications described above are based at least in part on the involvement of the mono- and disaccharide compounds in the modulation of Toll-like receptor activity. In particular, Toll-like receptors Tlr2, Tlr4, and others, are believed to be specifically activated, competitively inhibited or otherwise affected by the non-toxic LPS derivatives and mimetics disclosed herein. Accordingly, the methods of the invention provide a powerful and selective approach for modulating the innate immune response pathways in animals without giving rise to the toxicities often associated with the native bacterial components that normally stimulate those pathways.

Illustrative Mono- and Disaccharide Compounds

Illustrative mono- or disaccharide compounds employed in the above prophylactic and therapeutic applications comprise compounds having the formula:

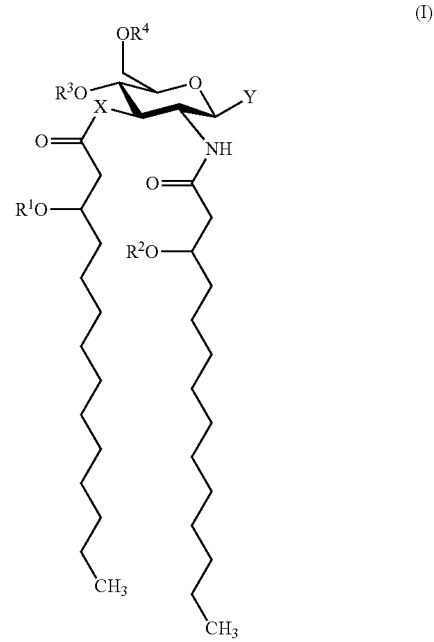

(I)

and pharmaceutically acceptable salts thereof, wherein X is —O— or —NH—; $R^1$ and $R^2$ are each independently a $(C_2\text{-}C_{24})$acyl group, including saturated, unsaturated and branched acyl groups; $R^3$ is —H or —$PO_3R^{11}R^{12}$ wherein $R^{11}$ and $R^{12}$ are each independently —H or $(C_1\text{ }C_4)$alkyl; $R^4$ is —H, =$CH_2$ or —$PO3R^{13}R^{14}$, wherein $R^{13}$ and $R^{14}$ are each independently selected from —H and $(C_1\text{ }C_4)$alkyl; and Y is a radical selected from the formulae:

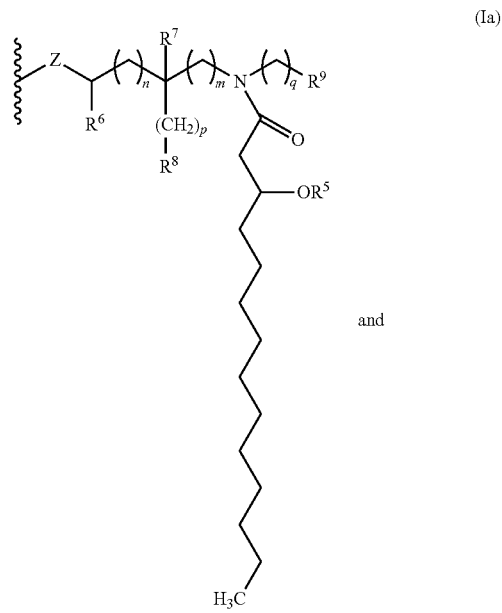

(Ia)

and

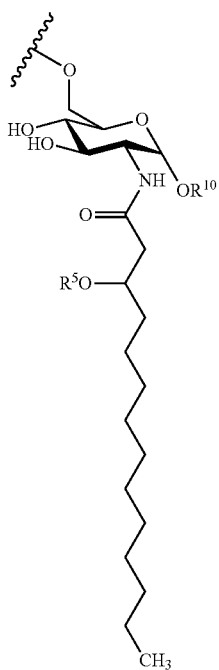

(Ib)

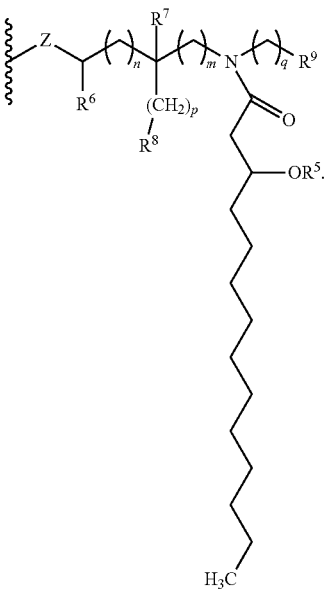

(Ia)

wherein the subscripts n, m, p and q are each independently an integer of from 0 to 6; $R^5$ is a $(C_2-C_{24})$acyl group (including, as above, saturated, unsaturated and branched acyl groups); $R^6$ and $R^7$ are independently selected from H and $CH_3$; $R^8$ and $R^9$ are independently selected from H, OH, $(C_1-C_4)$alkoxy, —$PO_3H_2$, —$OPO_3H_2$, —$SO_3H$, —$OSO_3H$, —$SR^{15}$, —CN, —$NO_2$, —CHO, —$CO_2R^{15}$, —$CONR^{15}R^{16}$, $PO_3R^{15}R^{16}$, —$OPO_3R^{15}R^{16}$, —$SO_3R^{15}$ and —$OSO_3R^{15}$, wherein $R^{15}$ and $R^{16}$ are each independently selected from H and $(C_1-C_4)$ alkyl; $R^{10}$ is selected from H, $CH_3$, —$PO_3H_2$, ω-phosphonooxy$(C_2-C_{24})$alkyl, and ω-carboxy$(C_1-C_{24})$alkyl; and Z is —O— or —S—; with the proviso that when $R^3$ is —$PO_3R^{11}R^{12}$, $R^4$ is other than —$PO_3R^{13}R^{14}$.

Additionally, when $R^3$ is —$PO_3H_2$, $R^4$ is H, $R^{10}$ is H, $R^1$ is n-tetradecanoyl, $R^2$ is n-octadecanoyl and $R^5$ is n-hexadecanoyl, then X is other than —O—.

In the general formula above, the configuration of the 3' stereogenic centers to which the normal fatty acid acyl residues are attached is R or S, but preferably R. The stereochemistry of the carbon atoms to which $R^6$ and $R^7$ are attached can be R or S. All stereoisomers, enantiomers, diastereomers and mixtures thereof are considered to be within the scope of the present invention.

In one group of preferred embodiments, Y has the formula:

Within this group of embodiments, the acyl groups $R^1$, $R^2$ and $R^5$ will be selected such that at least two of the groups are $(C_2-C_6)$acyl. Further preferred are those embodiments in which the total number of carbon atoms in $R^1$, $R^2$ and $R^5$ is from about 6 to about 22, more preferably about from about 12 to about 18. In other preferred embodiments, X is O and Z is O. The subscripts n, m, p and q are preferably integers of from 0 to 3, more preferably, 0 to 2. Of the remaining substituents, $R^6$ and $R^7$ are preferably H. The present invention further contemplates those embodiments in which the preferred substituents are combined in one molecule.

In another group of embodiments, $R^1$, $R^2$ and $R^5$ are selected from $(C_{12}-C_{20})$acyl with the proviso that the total number of carbon atoms in $R^1$, $R^2$ and $R^5$ is from about 44 to about 60. More preferably, the total number of carbon atoms in $R^1$, $R^2$ and $R^5$ is from about 46 to about 52. Still further preferred are those embodiments in which X and Z are both —O—.

In another group of embodiments, Y has the formula:

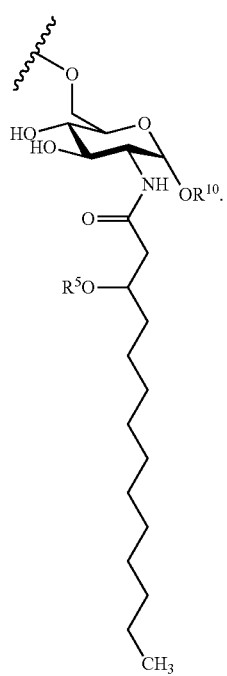

(Ib)

As with the preferred group of embodiments provided above, in this group the acyl groups $R^1$, $R^2$ and $R^5$ will also be selected such that at least two of the groups are $(C_2-C_6)$acyl. Further preferred are those embodiments in which the total number of carbon atoms in $R^1$, $R^2$ and $R^5$ is from about 6 to about 22, more preferably about from about 12 to about 18. In other preferred embodiments, X is O. Of the remaining substituents, $R^3$ is preferably phosphono ($-PO_3H_2$) and $R^4$ is preferably H. The present invention further contemplates those embodiments in which various combinations of the preferred substituents are combined in one molecule.

In another group of embodiments, $R^1$, $R^2$ and $R^5$ are selected from $(C_{12}-C_{24})$acyl with the proviso that the total number of carbon atoms in $R^1$, $R^2$ and $R^5$ is from about 44 to about 60. More preferably, the total number of carbon atoms in $R^1$, $R^2$ and $R^5$ is from about 46 to about 52. Particularly preferred fatty acid groups for $R^1$, $R^2$ and $R^5$ are normal $C_{14}$, $C_{16}$ and $C_{18}$ fatty acid groups. Still further preferred are those embodiments in which X is $-O-$. Similar to the shorter acyl chain embodiments provided above, $R^3$ is preferably phosphono ($-PO_3H_2$) and $R^4$ is preferably H.

In another preferred embodiments of the present invention, Y is a radical of formula (Ib), X is O, $R^3$ is phosphono, $R^4$ is H, and $R^1$, $R^2$ and $R^5$ are selected from $(C_{12}-C_{24})$acyl with the proviso that the total number of carbon atoms in $R^1$, $R^2$ and $R^5$ is from about 46 to about 52. Still further preferred are those compounds in which $R^2$ is $(C_{16}-C_{18})$acyl.

The term "alkyl" by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e., $C_1-C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Typically, an alkyl group will have from 1 to 24 carbon atoms. A "lower alkyl" or is a shorter chain alkyl group, generally having eight or fewer carbon atoms.

The terms "alkoxy", "alkylamino" and "alkylthio" (or thioalkoxy) are used in their conventional sense, and refer to those alkyl groups attached to the remainder of the molecule via an oxygen atom, an amino group, or a sulfur atom, respectively.

The term "acyl" refers to a group derived from an organic acid by removal of the hydroxy group. Examples of acyl groups include acetyl, propionyl, dodecanoyl, tetradecanoyl, isobutyryl, and the like. Accordingly, the term "acyl" is meant to include a group otherwise defined as $-C(O)$-alkyl.

Each of the above terms (e.g., "alkyl" "acyl") are meant to include both substituted and unsubstituted forms of the indicated radical. Preferred substituents for each type of radical are provided below.

Substituents for the alkyl and acyl radicals can be a variety of groups selected from: $-OR'$, $=O$, $=NR'$, $=N-OR'$, $-NR'R''$, $-SR'$, -halogen, $-SiR'R''R'''$, $-OC(O)R'$, $-C(O)R'$, $-CO_2R'$, $-CONR'R''$, $-OC(O)NR'R''$, $-NR''C(O)R'$, $-NR'C(O)NR''R'''$, $-NR''C(O)_2R'$, $-NH-C(NH_2)=NH$, $-NR'C(NH_2)=NH$, $-NHC(NH_2)=NR'$, $-S(O)R'$, $-S(O)_2R'$, $-S(O)_2NR'R''$, $-CN$ and $-NO_2$ in a number ranging from zero to (2 m'+1), where m' is the total number of carbon atoms in such radical. R', R'' and R''' each independently refer to hydrogen and unsubstituted $(C_1-C_8)$alkyl. When R' and R'' are attached to the same nitrogen atom, they can be combined with the nitrogen atom to form a 5-, 6-, or 7-membered ring. For example, $-NR'R''$ is meant to include 1-pyrrolidinyl and 4-morpholinyl. From the above discussion of substituents, one of skill in the art will understand that the term "alkyl" is meant to include groups such as haloalkyl (e.g., $-CF_3$ and $-CH_2CF_3$) and the like.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts," *Journal of Pharmaceutical Science,* 66, 1-19, 1977). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-$^{125}$ (125I) or carbon-14 ($^{14}C$). All isotopic variations of the compounds of the present invention, whether radioactive or not, are intended to be encompassed within the scope of the present invention.

The mono- and disaccharide compounds can be prepared by any suitable means, many of which have been described. For example, certain compounds useful in the present invention are described in co-pending application Ser. Nos. 08/853, 826, now U.S. Pat. No. 6,113,918; Ser. No. 09/439,839 (filed Nov. 12, 1999), now U.S. Pat. No. 6,303,347; and in PCT/US98/09385 (WO 98/50300, Oct. 12, 1998) the disclosures of which are incorporated herein by reference in their entireties. Other compounds can be prepared in a manner similar to that described for RC-552 (L34) in U.S. Pat. No. 6,013,640. Still other compounds can be prepared using methods outlined in Johnson, et al., *J. Med. Chem.* 42:4640-4649 (1999), Johnson, et al., *Bioorg. Med. Chem. Lett.* 9:2273-2278 (1999), and PCT/US98/50399 (WO 98/50399, Nov. 12, 1998). Still other compounds can be prepared according to, for example, U.S. Pat. Nos. 4,436,727; 4,877,611; 4,866,034; 4,912,094; and 4,987,237. In general, the synthetic methods described in the above-noted references and other synthetic methods otherwise familiar in the art are broadly applicable to the preparation these compounds. For example, in making compounds having different acyl groups and substitutions, one of skill in the art will appreciate that the convergent methods described therein can be modified to use alternate acylating agents, or can be initiated with commercially available materials having appropriate acyl groups attached.

Illustrative Pharmaceutical Compositions and their Delivery

In another embodiment, the present invention concerns pharmaceutical compositions comprising one or more of the mono- and disaccharide compounds disclosed herein in pharmaceutically-acceptable carriers/excipients for administration to a cell, tissue, animal or plant, either alone, or in combination with one or more other modalities of therapy. In a preferred embodiment, the pharmaceutical compositions are formulated in the absence of exogenous antigen, i.e., are used in monotherapeutic applications. For many such embodiments, the pharmaceutical compositions of the invention will comprise one or more of the monosaccharide compounds described herein.

Illustrative carriers for use in formulating the pharmaceutical compositions include, for example, oil-in-water or water-in-oil emulsions, aqueous compositions with or without inclusion of organic co-solvents suitable for intravenous (IV) use, liposomes or surfactant-containing vesicles, microspheres, microbeads and microsomes, powders, tablets, capsules, suppositories, aqueous suspensions, aerosols, and other carriers apparent to one of ordinary skill in the art.

In certain embodiments, the pharmaceutical compositions will comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives.

For certain applications, aqueous formulations will be preferred, particularly those comprising an effective amount of one or more surfactants. For example, the composition can be in the form of a micellar dispersion comprising at least one suitable surfactant, e.g., a phospholipid surfactant. Illustrative examples of phospholipids include diacyl phosphatidyl glycerols, such as dimyristoyl phosphatidyl glycerol (DPMG), dipalmitoyl phosphatidyl glycerol (DPPG), and distearoyl phosphatidyl glycerol (DSPG), diacyl phosphatidyl cholines, such as dimyristoyl phosphatidylcholine (DPMC), dipalmitoyl phosphatidylcholine (DPPC), and distearoyl phosphatidylcholine (DSPC); diacyl phosphatidic acids, such as dimyristoyl phosphatidic acid (DPMA), dipalmitoyl phosphatidic acid (DPPA), and distearoyl phosphatidic acid (DSPA); and diacyl phosphatidyl ethanolamines such as dimyristoyl phosphatidyl ethanolamine (DPME), dipalmitoyl phosphatidyl ethanolamine (DPPE) and distearoyl phosphatidyl ethanolamine (DSPE). Typically, a surfactant:mono-/disaccharide molar ratio in an aqueous formulation will be from about 10:1 to about 1:10, more typically from about 5:1 to about 1:5, however any effective amount of surfactant may be used in an aqueous formulation to best suit the specific objectives of interest.

The compounds and pharmaceutical compositions of the invention can be formulated for essentially any route of administration, e.g., injection, inhalation by oral or intranasal routes, rectal, vaginal or intratracheal instillation, ingestion, or transdermal or transmucosal routes, and the like. In this way, the therapeutic effects attainable by the methods and compositions of the invention can be, for example, systemic, local, tissue-specific, etc., depending of the specific needs of a given application of the invention.

Illustrative formulations can be prepared and administered parenterally, i.e., intraperitoneally, subcutaneously, intramuscularly or intravenously. One illustrative example of a carrier for intravenous use includes a mixture of 10% USP ethanol, 40% USP propylene glycol or polyethylene glycol 600 and the balance USP Water for Injection (WFI). Other illustrative carriers include 10% USP ethanol and USP WFI; 0.01-0.1% triethanolamine in USP WFI; or 0.01-0.2% dipalmitoyl diphosphatidylcholine in USP WFI; and 1-10% squalene or parenteral vegetable oil-in-water emulsion. Pharmaceutically acceptable parenteral solvents will generally be selected such that they provide a solution or dispersion which may be filtered through a 0.22 micron filter without removing the active ingredient.

Illustrative examples of carriers for subcutaneous or intramuscular use include phosphate buffered saline (PBS) solution, 5% dextrose in WFI and 0.01-0.1% triethanolamine in 5% dextrose or 0.9% sodium chloride in USP WFI, or a 1 to 2 or 1 to 4 mixture of 10% USP ethanol, 40% propylene glycol and the balance an acceptable isotonic solution such as 5% dextrose or 0.9% sodium chloride; or 0.01-0.2% dipalmitoyl diphosphatidylcholine in USP WFI and 1 to 10% squalene or parenteral vegetable oil-in-water emulsions.

Examples of carriers for administration via mucosal surfaces depend upon the particular route, e.g., oral, sublingual, intranasal, etc. When administered orally, illustrative examples include pharmaceutical grades of mannitol, starch, lactose, magnesium stearate, sodium saccharide, cellulose, magnesium carbonate and the like, with mannitol being preferred. When administered intranasally, illustrative examples include polyethylene glycol, phospholipids, glycols and glycolipids, sucrose, and/or methylcellulose, powder suspensions with or without bulking agents such as lactose and preservatives such as benzalkonium chloride, EDTA. In a particularly illustrative embodiment, the phospholipid 1,2 dipalmitoyl-sn-glycero-3-phosphocholine (DPPC) is used as an isotonic aqueous carrier at about 0.01-0.2% for intranasal administration of the compound of the subject invention at a concentration of about 0.1 to 3.0 mg/ml.

When administered by inhalation, illustrative carriers include polyethylene glycol or glycols, DPPC, methylcellulose, powdered dispersing agents, and preservatives, with polyethylene glycols and DPPC being preferred. In many instances, it will be preferred that the mono- or disaccharide compounds be in a nebulized form when administration by inhalation. Illustratively, delivery may be by use of a single-use delivery device, a mist nebulizer, a breath-activated powder inhaler, an aerosol metered-dose inhaler (MDI) or any other of the numerous nebulizer delivery devices available in the art. Additionally, mist tents or direct administration through endotracheal tubes may also be used. Delivery via an intratracheal or nasopharyngeal mode will be efficacious for certain indications.

One skilled in this art will recognize that the above description is illustrative rather than exhaustive. Indeed, many additional formulations techniques and pharmaceutically-acceptable excipients and carrier solutions are well-known to those skilled in the art, as is the development of suitable dosing and treatment regimens for using the particular compositions described herein in a variety of treatment regimens.

The compounds can be evaluated in a variety of assay formats to identify and select those having the characteristics best suited for a given application of the invention. For example, animal models can be used for identifying and evaluating cytokine release profiles into systemic circulation following administration of a mono- and/or disaccharide compound. In addition, various in vitro and in vivo models exist for examining changes in one or more aspects of an immune response to different antigenic components in order to identify compounds best suited for eliciting a specific immune response of interest. For example, a compound can be contacted with target cells, such as macrophages, dendritic cells or Langerhans cells in vitro, and elaborated cytokines can be measured. In addition, gene expression arrays can be used to identify specific pathways activated or inhibited by a particular mono- or disaccharide of interest.

It will be understood that, if desired, the compounds disclosed herein may be administered in combination with other therapeutic modalities, such as antimicrobial, antiviral and antifungal compounds or therapies, various DNA-based therapeutics, RNA-based therapeutics, polypeptide-based therapeutics. and/or with other immunoeffectors. In fact, essentially any other component may also be included, given that the additional component(s) do not cause a significant adverse effect upon contact with the target cells or host tissues. The compositions may thus be delivered along with various other agents as required or desired for the specific embodiment(s) of the invention being implemented.

Illustratively, the pharmaceutical compositions of the invention can include, or be used in conjunction with, DNA encoding one or more therapeutic proteins, antisense RNAs, ribozymes or the like. The DNA may be present within any of a variety of delivery systems known to those of ordinary skill in the art, including nucleic acid expression systems, bacteria and viral expression systems. Numerous gene delivery techniques are well known in the art, such as those described by Rolland, *Crit. Rev. Therap. Drug Carrier Systems* 15:143-198, 1998, and references cited therein. Appropriate nucleic acid expression systems contain the necessary DNA sequences for expression in the patient (such as a suitable promoter and terminating signal). In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *Proc. Natl. Acad. Sci. USA* 86:317-321, 1989; Flexner et al., *Ann. N.Y. Acad. Sci.* 569:86 103, 1989; Flexner et al., *Vaccine* 8:17 21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616 627, 1988; Rosenfeld et al., *Science* 252:431434, 1991; Kolls et al., *Proc. Natl. Acad. Sci, USA* 91:215 219, 1994; Kass Eisler et al., *Proc. Natl. Acad. Sci. USA* 90:11498 11502, 1993; Guzman et al., *Circulation* 88:2838 2848, 1993; and Guzman et al., *Cir. Res.* 73:1202 1207, 1993. Techniques for incorporating DNA into such expression systems are well known to those of ordinary skill in the art.

The DNA may also be "naked," as described, for example, in Ulmer et al., *Science* 259:1745-1749, 1993 and reviewed by Cohen, *Science* 259:1691-1692, 1993. The uptake of naked DNA may be increased by coating the DNA onto biodegradable beads, which are efficiently transported into the cells. It will be apparent that a pharmaceutical composition of the invention may comprise both a polynucleotide and a protein component.

Any of a variety of additional immunostimulants may be included in the compositions of this invention. For example, cytokines, such as GM-CSF, interferons or interleukins to further modulate an immune response of interest. For example, in certain embodiments, additional components may be included in the compositions to further enhance the induction of high levels of Th1-type cytokines (e.g., IFN-$\gamma$, TNF$\alpha$, IL-2 and IL-12). Alternatively, or in addition, high levels of Th2-type cytokines (e.g., IL-4, IL-5, IL-6 and IL-10) may be desired for certain therapeutic applications. The levels of these cytokines may be readily assessed using standard assays. For a review of the families of cytokines, see Mosmann and Coffman, *Ann. Rev. Immunol.* 7:145-173, 1989.

Illustrative compositions for use in induction of Th1-type cytokines include, for example, a combination of CpG-containing oligonucleotides (in which the CpG dinucleotide is unmethylated) as described, for example, in WO 96/02555, WO 99/33488 and U.S. Pat. Nos. 6,008,200 and 5,856,462. Immunostimulatory DNA sequences are also described, for example, by Sato et al., *Science* 273:352, 1996. Other suitable immunostimulants comprise saponins, such as QS21 (Aquila Biopharmaceuticals Inc., Framingham, Mass.), and related saponin deriviatives and mimetics thereof.

Other illustrative immunostimulants that can be used in conjunction with the present invention include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), and Enhanzyn™ immunostimulant (Corixa, Hamilton, Mont.). Polyoxyethylene ether immunostimulants, are described in WO 99/52549A1.

GENERAL DEFINITIONS

As used herein, "an effective amount" is that amount which shows a response over and above the vehicle or negative controls. As discussed above, the precise dosage of the compound of the subject invention to be administered to a patient will depend the route of administration, the pharmaceutical composition, and the patient.

The phrase "pharmaceutically acceptable" refers to molecular entities and compositions that do not produce an allergic or similar untoward reaction when administered to a human.

As used herein, "carrier" or "excipient" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

EXAMPLES

Example 1

Protection Against *P. carinii* Infection by Prophylactic Administration of Monophosphoryl Lipid A Mice were pretreated with L3T4 anti-CD4 antibody for a minimum of 2 weeks (2 injections/week, 0.2 mg/injection) or until the peripheral CD4 count was reduced by at least about 50%.

An aqueous formulation was prepared containing 1 mg/ml 3-O-deacylated monophosphoryl lipid A and 108 µg/ml of the surfactant DPPC in water. The formulation was administered intratracheally via a small cannula at −24 hours and then twice a week for the remainder of the study. The concentrations administered are indicated below in Table 1. One million *P. carinii* were inoculated trans-tracheally at day 0. Twice-weekly treatments were continued for 7 weeks, lungs were removed and impression smears made. Slides were stained with Giemsa and silver and scored for the presence of *P. carinii* as follows.

| Score | 5 | >100/1000x field |
|---|---|---|
| | 4 | 10-100/field |
| | 3 | 1-10/field |
| | 2 | 1-10/10 fields |
| | 1 | 1-10/50 fields |
| | 0 | 0/50 fields |

The results of these experiments are summarized below in Table 1:

TABLE 1

| | GIEMSA | SILVER |
|---|---|---|
| PLACEBO GROUP | 3.3 ± 0.7 | 2.5 ± 0.4 |
| 25 MG/KG | 3.4 ± 0.5 | 3.3 ± 0.1 |
| 100 MG/KG | 2.7 ± 0.5 | 3.2 ± 0.1 |
| 250 MG/KG | 1.8 ± 0.8 | 1.6 ± 0.2 |

This study was repeated and the following results were obtained (Table 2):

TABLE 2

| | GIEMSA |
|---|---|
| PLACEBO GROUP | 3.3 ± 0.2 |
| UNTREATED CONTROL | 3.1 ± 0.3 |
| 100 MG/KG | 1.3 ± 0.3 |
| 200 MG/KG | 1.0 ± 0.3 |

These results demonstrate that pulmonary delivery of monophosphoryl lipid A promotes nonspecific resistance to infection by *Pneumocystis carinii* in immunocompromised mice. Inhalation of monophosphoryl lipid A led to activation of the local (and distal) innate immune responses resulting in enhanced nonspecific protection. Monophosphoryl lipid A mediated this protection primarily through activation of antigen presenting cells leading to increased phagocytic activity and the release of immuno-stimulatory cytokines. FACS analysis of cell lavaged from the lungs displayed markers for activated neutrophils but was unremarkable for an influx of leukocytes characteristic of a massive inflammatory response (ARDS). Analysis of spleen cells showed negative expression of CD11b or CD69, suggesting that the monophosphoryl lipid A formulations and the effects in this application were not systemic but were confined to the lung.

Example 2

Protection Against Lethal Influenza Challenge by Prophylactic Administration of Monophosphoryl Lipid A A dose of 20 µg MonoPhosphoryl Lipid A (MPL) was given to groups of female BALB/c mice by intranasal (i.n.) administration either 2 days prior to or the day of lethal influenza challenge. All mice were challenged with approximately 2 LD50 infectious influenza A/HK/68 administered i.n. Mortality was monitored for 21 days following influenza challenge. The results of these experiments is presented in FIG. 1. These data demonstrate that intranasal delivery of monophosphoryl lipid A promotes nonspecific resistance to infection by lethal influenza challenge in mice.

Example 3

Clinical Symptoms Following Intranasal Administration of L-Seryl Aminalkyl Glucosaminide Phosphates (AGPs)

A series of L-Seryl Aminoalkyl Glucosaminide Phosphate compounds (AGPs) was prepared as described in U.S. Pat. No. 6,113,918, issued Sep. 5, 2000, and in U.S. patent application Ser. No. 09/439,839, filed Nov. 12, 1999, now U.S. Pat. No. 6,303,347, each of which is incorporated herein by reference in its entirety.

Figure 2:
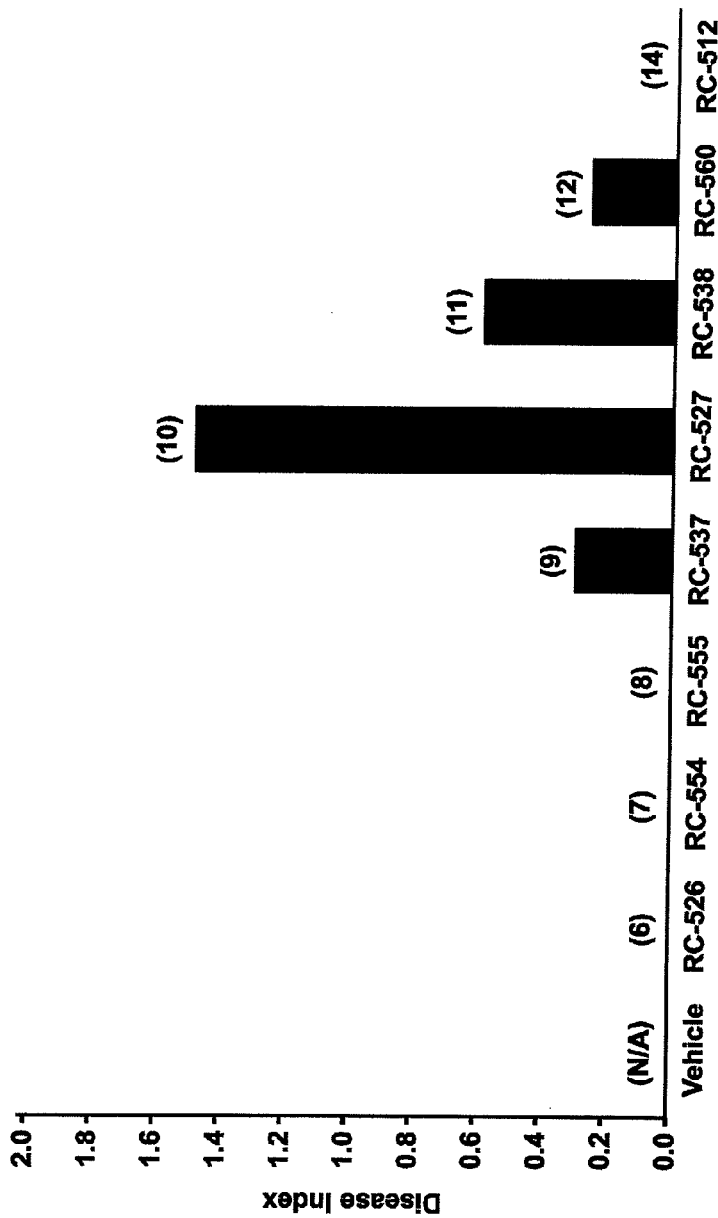
FIG. 2 is a graph depicting clinical symptoms following intranasal administration of L-Seryl Aminoalkyl Glucosaminide Phosphates (AGPs) to mice.

A dose of 20 µg of L-Seryl AGPs (RC-526, RC-554, RC-555, RC-537, RC-527, RC-538, RC-560, RC-512 and vehicle only) was given to groups of female BALB/c mice by intranasal (i.n.) administration. During the initial 4 days following AGP administration, the mice were monitored for three subjective indicators of disease (i.e. disease index) including observing ruffled fur, hunched posture and labored breathing. The results of these experiments is presented in FIG. 2. These data indicated that i.n. administration of the RC-537, RC-527, RC-538 and RC-560 induce some toxicity in mice at the given dose of 20 µg.

Example 4

Figure 3:
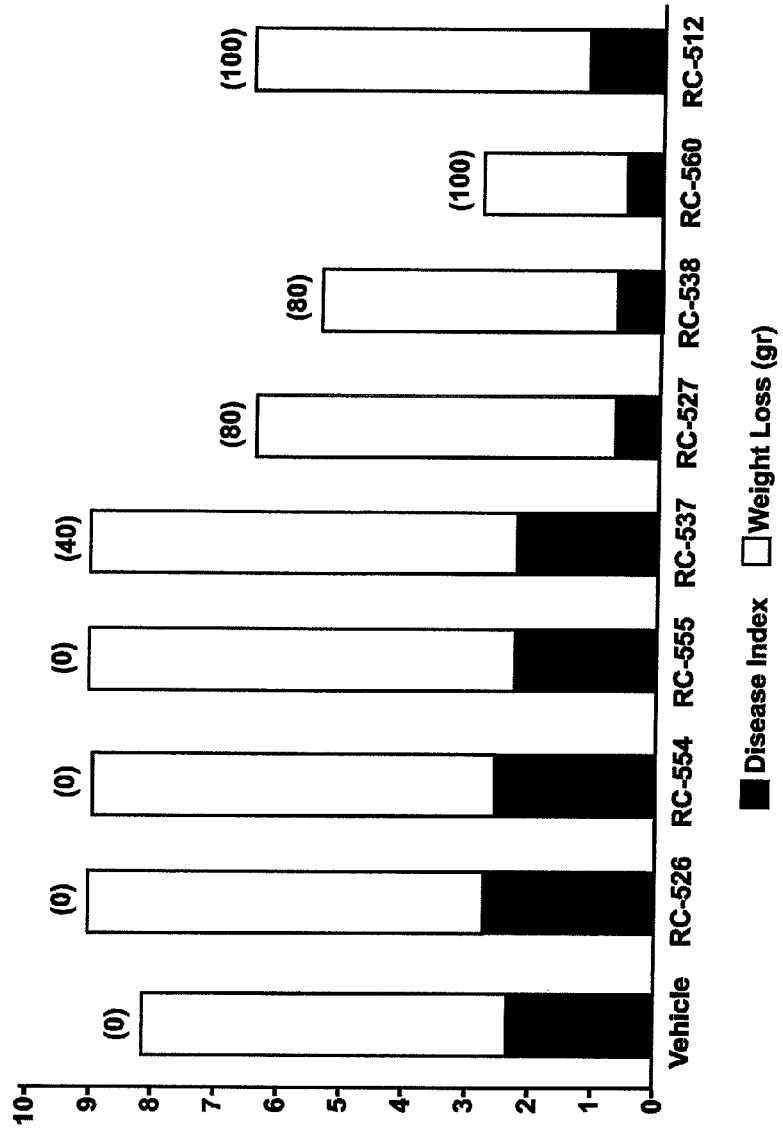
FIG. 3 is a graph depicting clinical symptoms following L-Seryl Aminoalkyl Glucosaminide Phosphates (AGPs) monotherapy and influenza challenge.
Figure 4A:
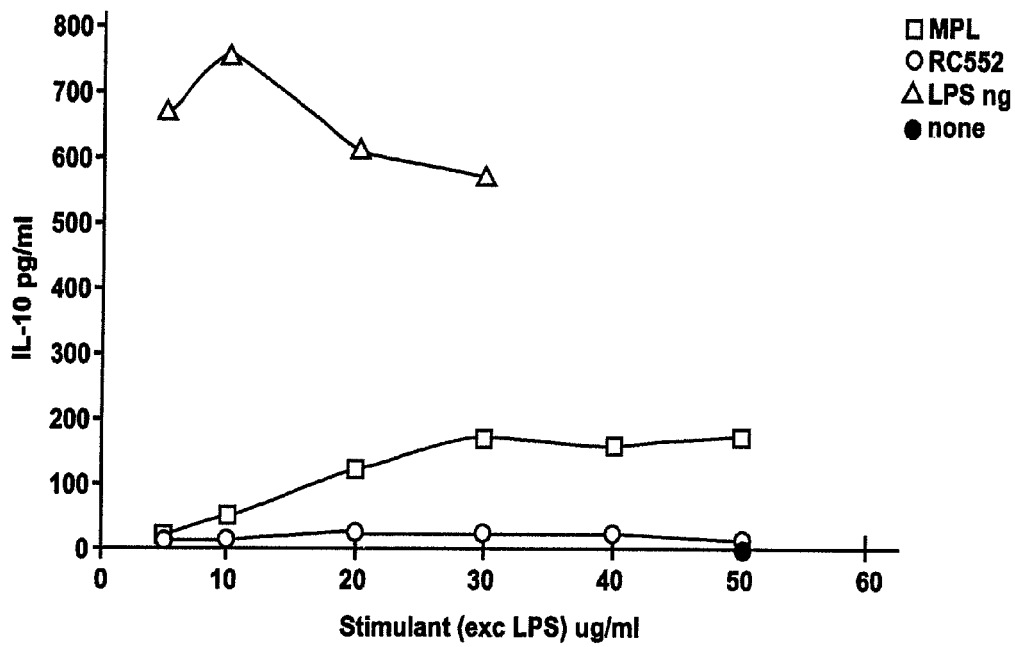
FIGS. 4-6 are graphs depicting cytokine induction by RC522 as compared to MPL in overnight whole blood cultures from three human donors (donors A-C, respectively).
Figure 4B:
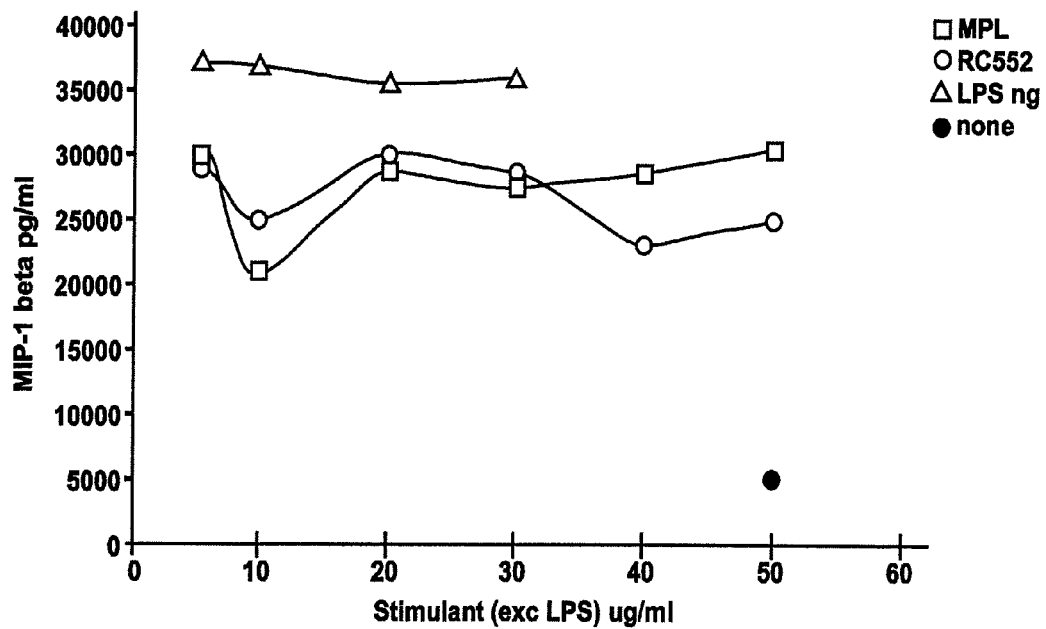
Figure 4C:
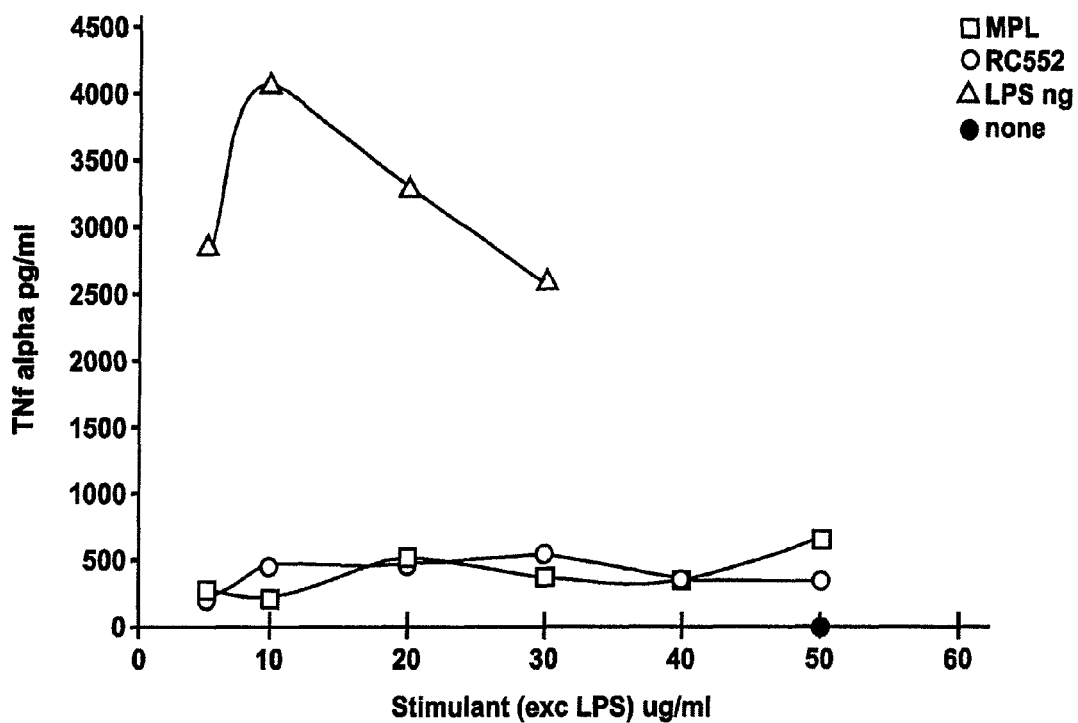
Figure 4D:
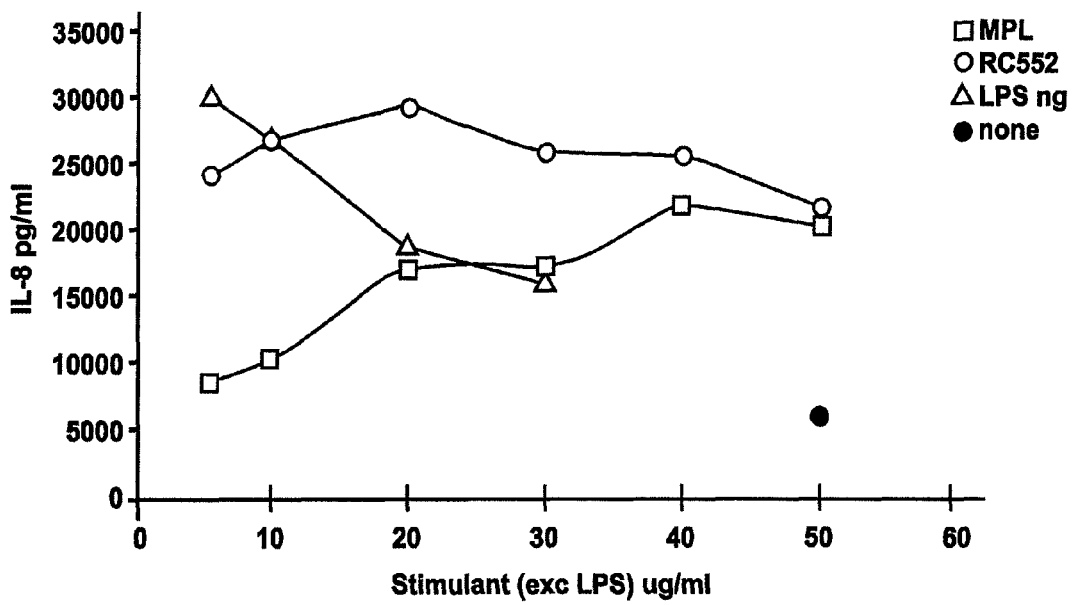
Figure 5A:
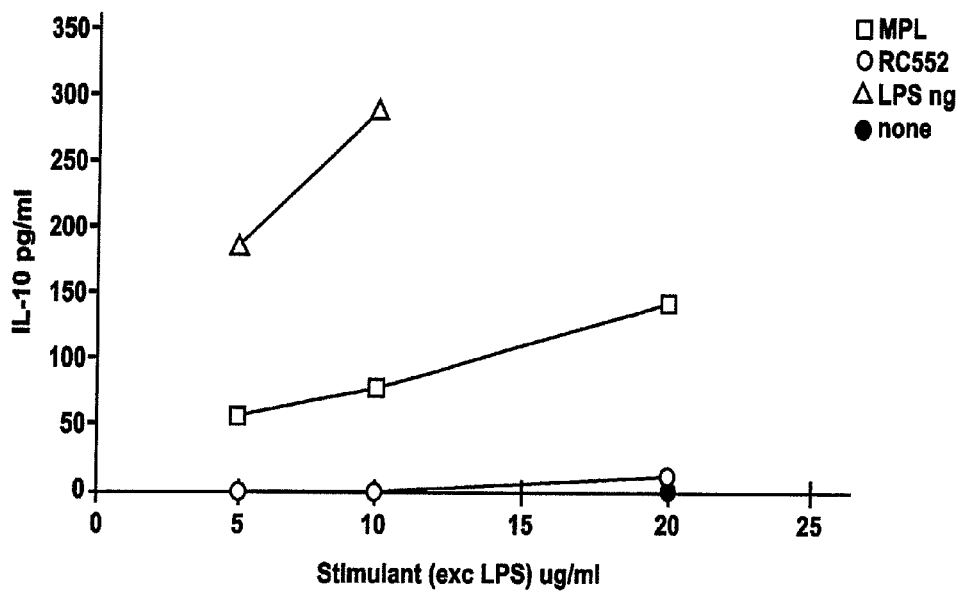
Figure 5B:
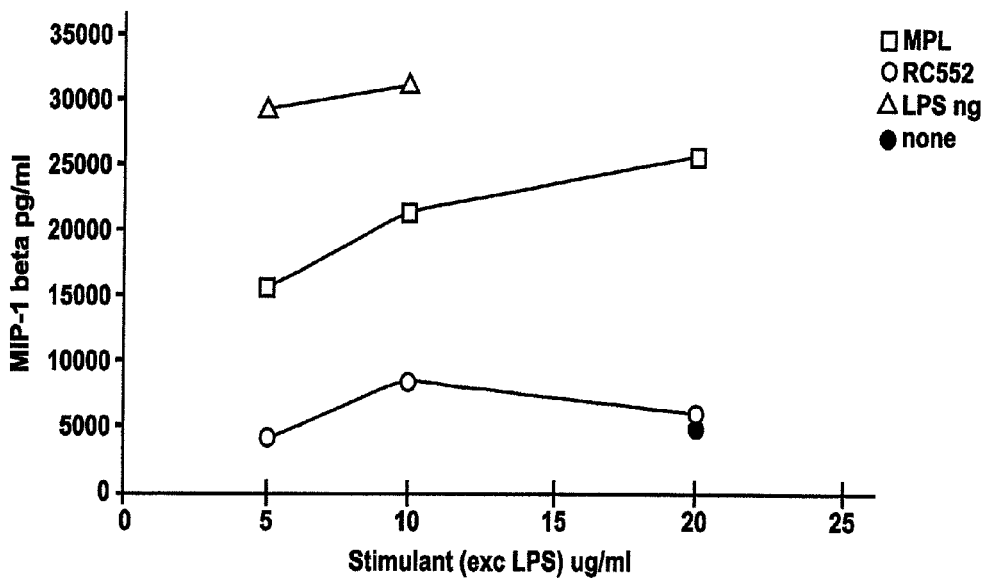
Figure 5C:
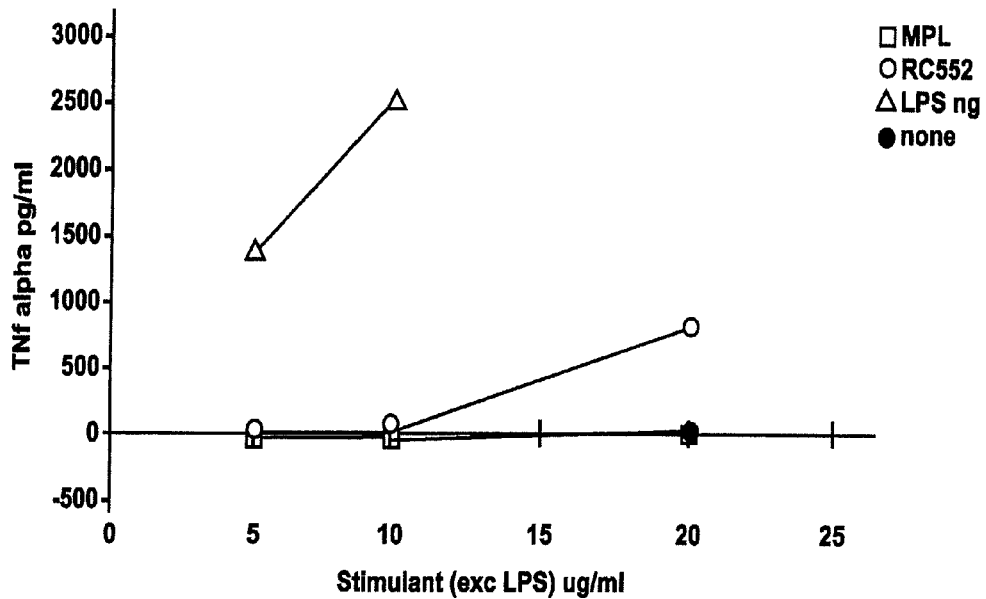
Figure 5D:
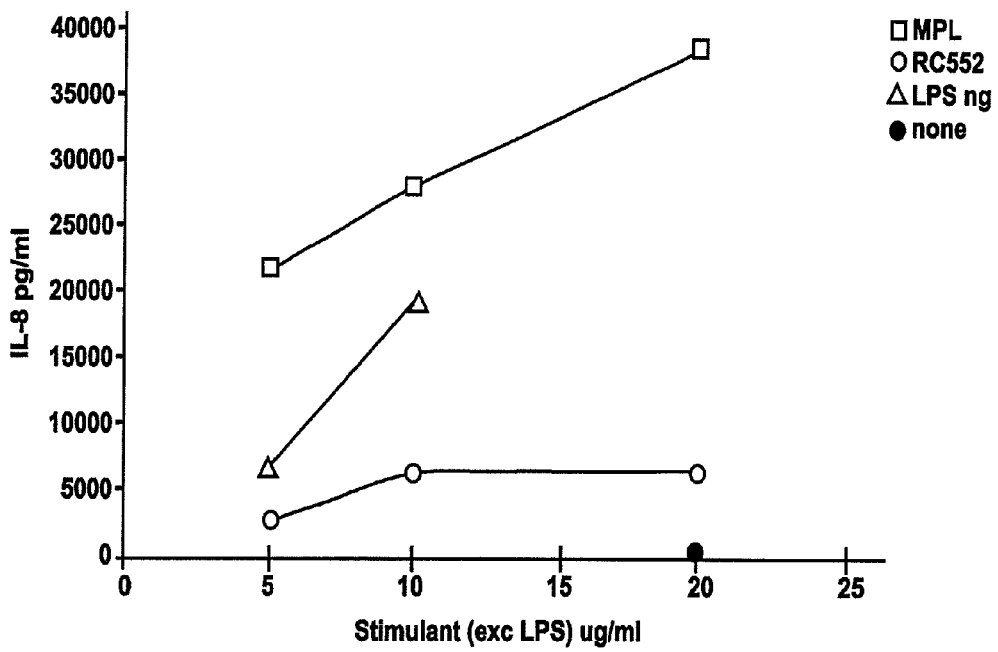
Figure 6A:
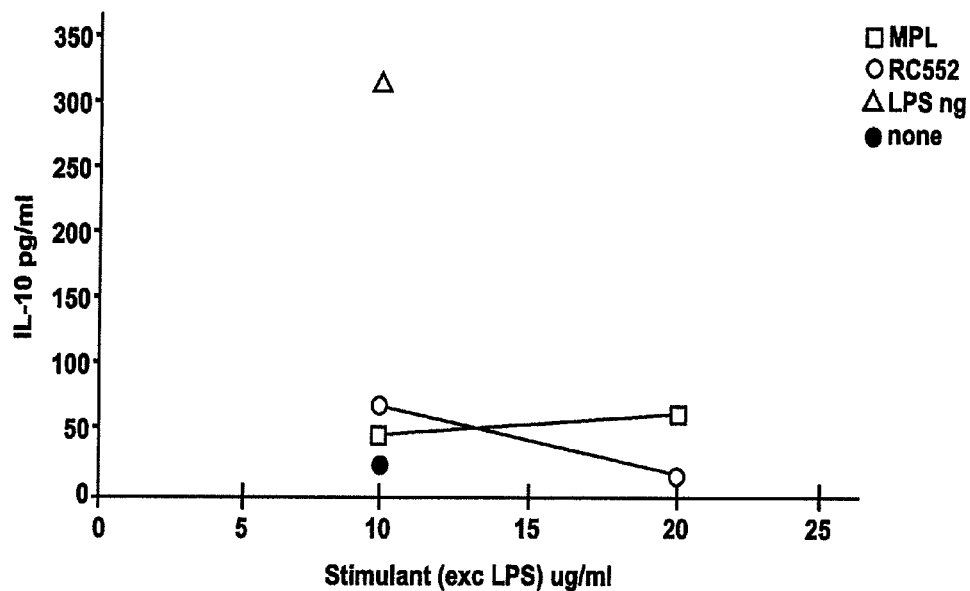
Figure 6B:
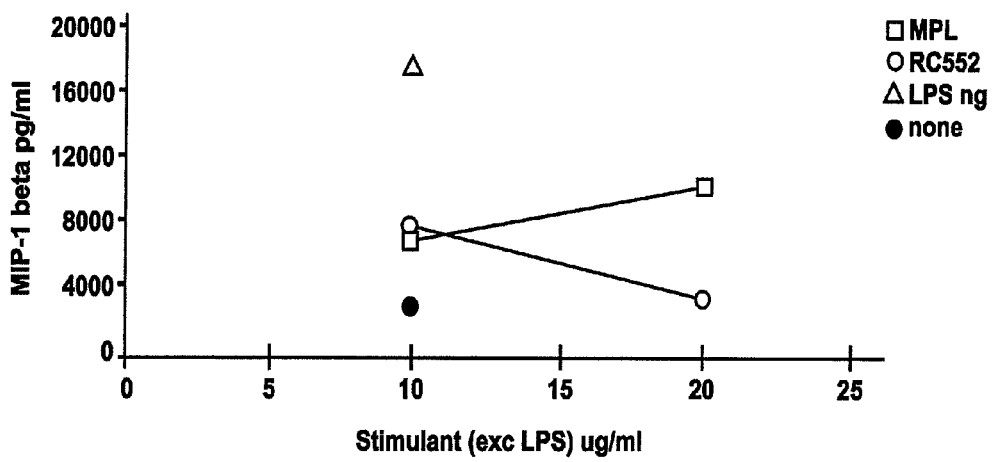
Figure 6C:
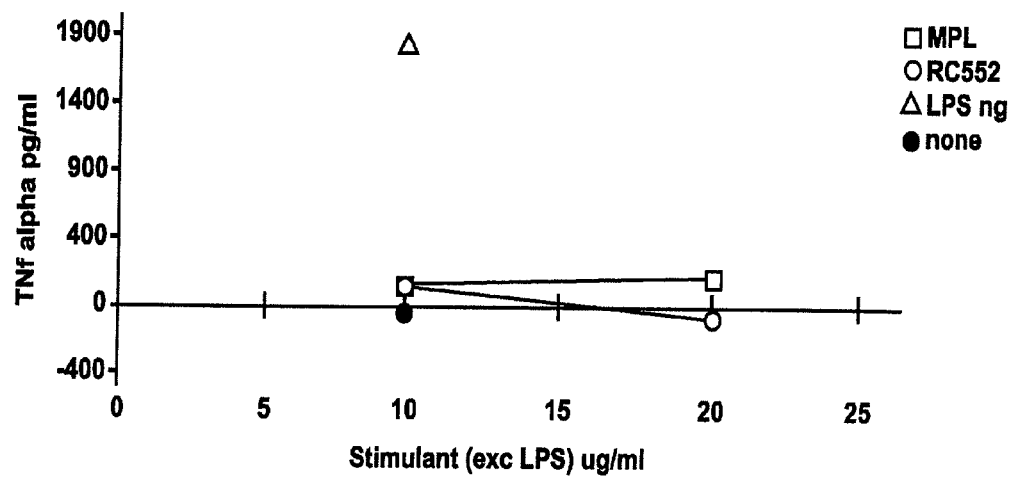
Figure 6D:
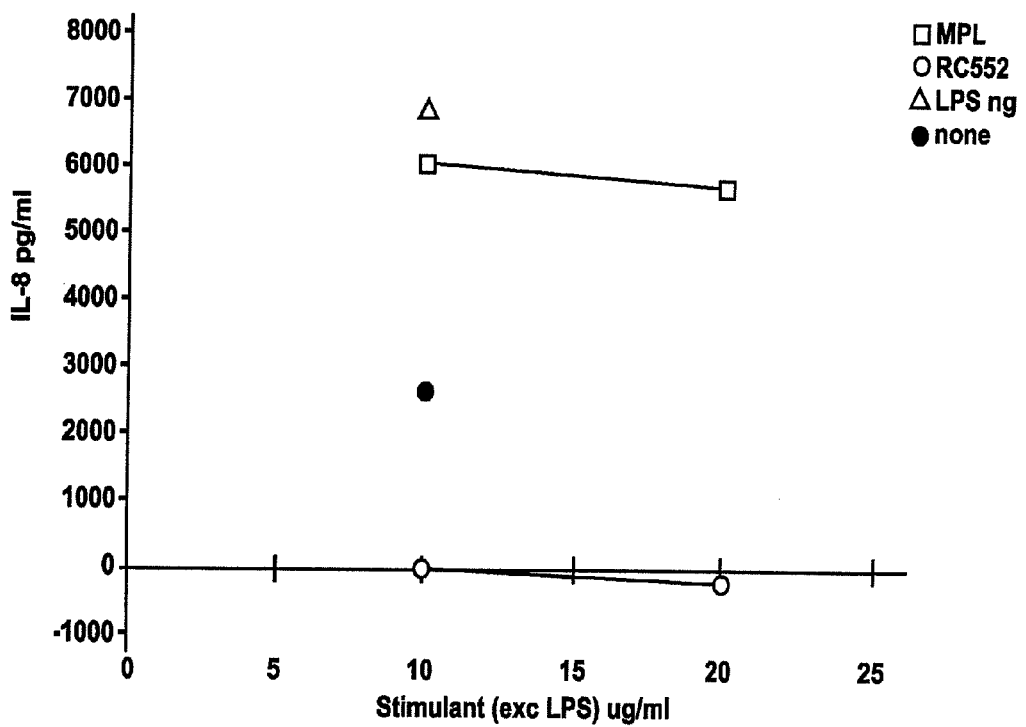

Clinical Symptoms Following Intranasal Administration of L-Seryl Aminalkyl Glucosaminide Phosphates (AGPs) and Influenza Challenge A dose of 20 µg L-Seryl AGPs (RC-526, RC-554, RC-555, RC-537, RC-527, RC-538, RC-560, RC-512 and vehicle only) was given to groups of female BALB/c mice by intranasal (i.n.) administration 2 days prior to or the day of lethal influenza challenge. All mice were challenged with approximately 2 LD50 infectious influenza A/HK/68 administered i.n. The disease index (ruffled fur, hunched posture and labored breathing) was monitored during days 4-19 following influenza challenge. Weight loss and mortality were monitored for 21 days following influenza challenge. The results of these experiments are presented in FIG. 3.

These data demonstrated the efficacy of AGP compounds RC-538, RC560 and RC-512 in providing substantial protection against influenza challenge.

L-Seryl AGPs having 14 carbon fatty acid chains in the primary fatty acid position and 6 to 14 carbon fatty acids chains in the secondary fatty acid position, (RC-526, RC-554, RC-555, RC-537, RC-527, RC-538, RC-560, RC-512, see FIG. 10), or combinations of 6 or 10 carbon fatty acids in the three secondary fatty acid positions, (RC-570, RC-568, RC-567, RC-566, RC-565, RC-569, see FIG. 10) were tested against MPL in the influenza challenge model as described above.

Figure 11:
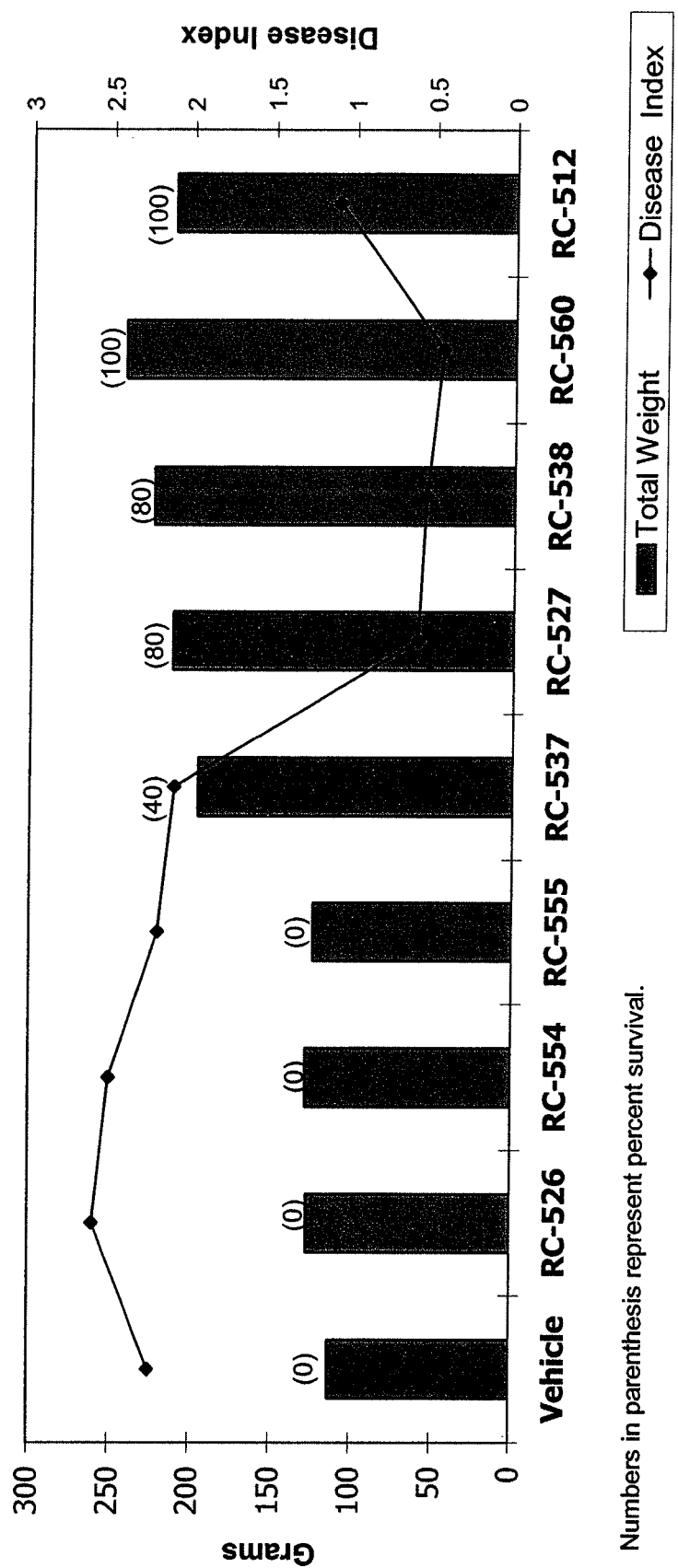
FIG. 11 is a graph showing clinical symptoms following intranasal administration of L-Seryl Aminoalkyl Glucosaminide Phosphates monotherapy and influenza challenge.
Figure 13:
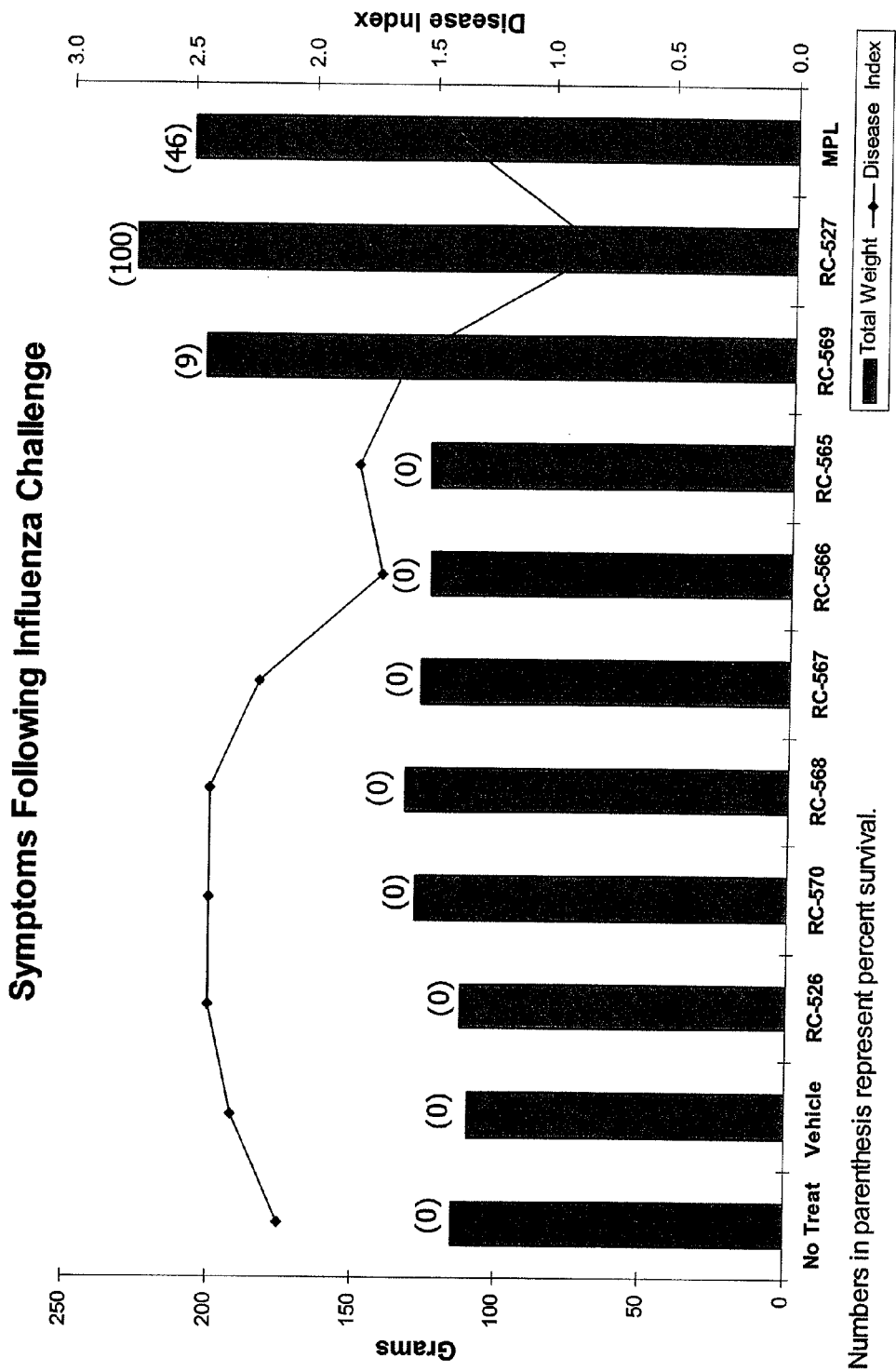
FIG. 13 is a graph showing clinical symptoms following intranasal administration of L-Seryl Aminoalkyl Glucosaminide Phosphates monotherapy and influenza challenge. L-Seryl compounds have various combinations of 6 and 10 carbon fatty acid chains in the secondary fatty acid position.

The results indicate that chain length and position have an effect on survival and disease severity. Treatment with AGP compounds having secondary fatty acid chains containing 9 or more carbons provided more protection against the influenza challenge than did those with smaller fatty acid chains. (FIG. 11). Length of the fatty acid chain rather than the dose administered, is most influential on survival, (FIG. 12). RC-526 (6 carbon chain) showed no difference in protection up to doses of 40 µg. RC-527 (10 carbon chain) provided maximum protection over a dose range of 2.5 µg to 40 µg. Additionally, those compounds having at least two 10 carbon fatty acid chains (RC-565 and RC-569) were more protective than those having fewer. (FIG. 13).

Example 5

Comparison of RC552 and MPL Using Human Whole Blood Cultures and Mouse Splenic Cultures This Example discloses cytokine induction by the synthetic lipid A compound RC552 as compared to the modified natural substance monophosphoryl lipid A (MPL) using human whole blood cultures and mouse splenocyte culture.

Lipid A compounds were tested by reconstitution in 0.2% triethanolamine in sterile water for irrigation, incubated at 56° C. and sonicated for 2×10 minutes at 37° C. LPS 055B5 (Sigma-Aldrich; St Louis, Mo.) was diluted into PBS.

Compounds were added to 450 µl of human whole blood and incubated with agitation for 5 to 24 hours. Three donors were selected (FIGS. 4-6, donors A-C, respectively). Supernatants were collected by centrifugation and diluted to 1/2 with an equal volume of PBS. (This dilution was not considered a dilution factor for cytokine calculations). Cytokine elaboration was measured by ELISA (R&D Systems; Minneapolis, Minn.) using the required volume of supernatant at full strength or diluted as much as ten fold.

BALB/c, DBA/2 and C3H/HEJ mice were purchased from The Jackson Laboratory (Bar Harbor, Me.). Spleens were taken from the mice between 2 PM and 3 PM, and separate single cell suspensions were obtained for each mouse strain. Red blood cells were lysed using Tris-ammonium chloride solution (Sigma-Aldrich), cells were washed and counted using Trypan Blue (Sigma-Aldrich) exclusion. One million splenocytes were cultured per well in 1.0 mL of culture medium. Splenic culture medium (SCM) was designed for 5 day or longer cultures of mouse splenocytes and consisted of RPMI 1640 (Sigma-Aldrich) supplemented to 5% with fetal bovine serum (HyClone; Logan, Utah), 100 ug/mL Gentamicin (Sigma-Aldrich), 250 ng/mL amphothericin (InVitrogen Life Technologies; Carlsbad, Calif.), 1×ITS (bovine insulin 500 ng/mL, human transferring 500 ng/mLg, sodium selenite 250 ng/mL, Sigma), beta-mercaptoethanol 43 nM (Sigma-Aldrich) purivic acid 1 mM (Sigma-Aldrich), HEPES 10 mM (Sigma-Aldrich). Data from these experiments is presented herein as FIG. 8.

Using human whole blood cultures, four cytokines were measured: IL-10, MIP-1 beta, TNF alpha, and IL-8. Two donors were tested once and one donor was tested twice. It is noteworthy that the donor who was tested twice had very high background TNF alpha at one test, but very low background TNF alpha one month later. Significant, however, is the time span of culture. High background TNF alpha was obtained with a 5.5 hour culture, and low background TNF alpha was obtained with an overnight, about 24 hour, culture. Nonetheless, even the 5.5 hour-low background culture was higher (about 600 pg/ml) than obtained in some previous cultures (518.2 pg/ml in a 5 hr test; 417 pg/ml in a 4 hr test; zero pg/ml 4 hr, low responder).

RC552 was similar to MPL for elaboration of TNF alpha in two of three 24 hours cultures, and one 5.5 hour culture. IL-8 induction, however, by RC552 was different than that for MPL in three of three cases. IL-8 induction by RC552 was lessened for two overnight cultures compared to MPL, but greater than MPL in one overnight culture.

For overnight cultures, IL-10 induction by RC552 was less than that for MPL. MIP-1 beta induction was lessened in one of 3 cases of overnight culture.

BALB/c responses and C3H/HEJ responses were compared for MPL and RC552. C3H/HEJ mice are genetic hyporesponders to LPS due to a mutation in toll-receptor 4. In these cultures, an oligonucleotide stimulant was used as a positive control for C3H/HEJ cultures. This oligonucleotide induced large amounts of IL-6 in BALB/c mice (1000 pg/mL) and in C3H/HEJ mice (488.5 pg/mL). Similarly, MIP-1 beta was induced in BALB/c and C3H/HEJ cultures (589 pg/mL and 554 pg/mL), as was IL-10 (342 pg/mL and 609 pg/mL), and TNF alpha (204 pg/mL and 30 pg/mL) in response to 10 ug/mL MPL or RC552, respectively.

Neither MPL nor RC552 induced a cytokine response using C3H/HEJ splenocytes. In BALB/c splenocyte cultures, however, IL-10, MIP-1 beta, TNF alpha and IL-6 were induced. RC552 induced less MIP-1 beta, TNF alpha and IL-6 than did MPL at the same concentrations. RC552 induced very little IL-10 (10.4 to 11.6 pg/mL) compared to MPL (1144.1 to 176.6 pg/mL).

Figure 7A:
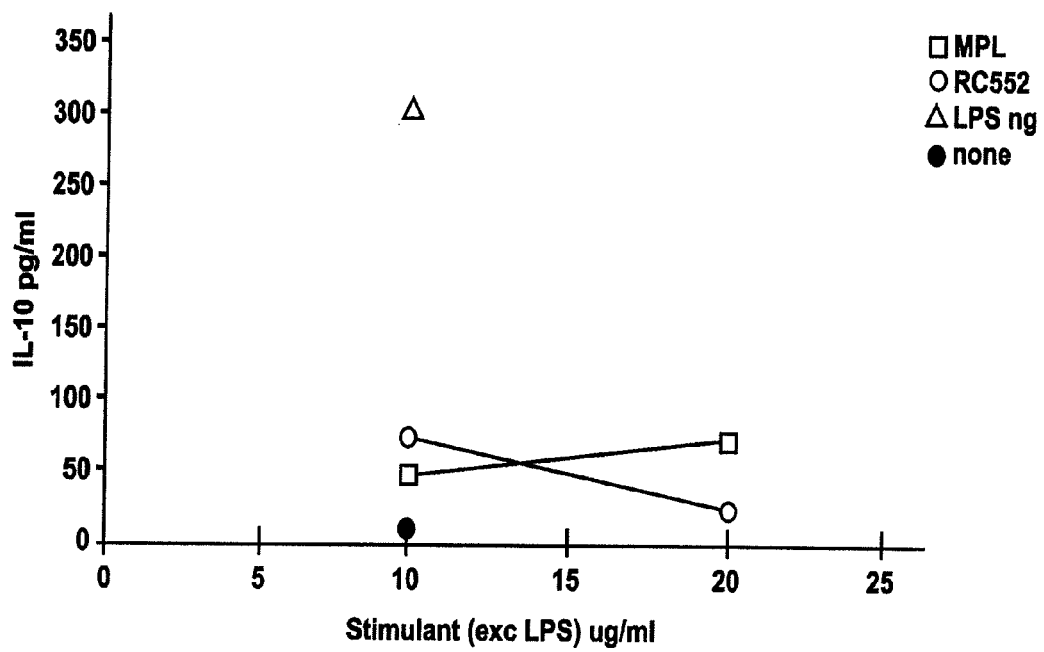
FIG. 7 are graphs depicting cytokine induction by RC522 as compared to MPL in short term whole blood cultures from donor A.
Figure 7B:
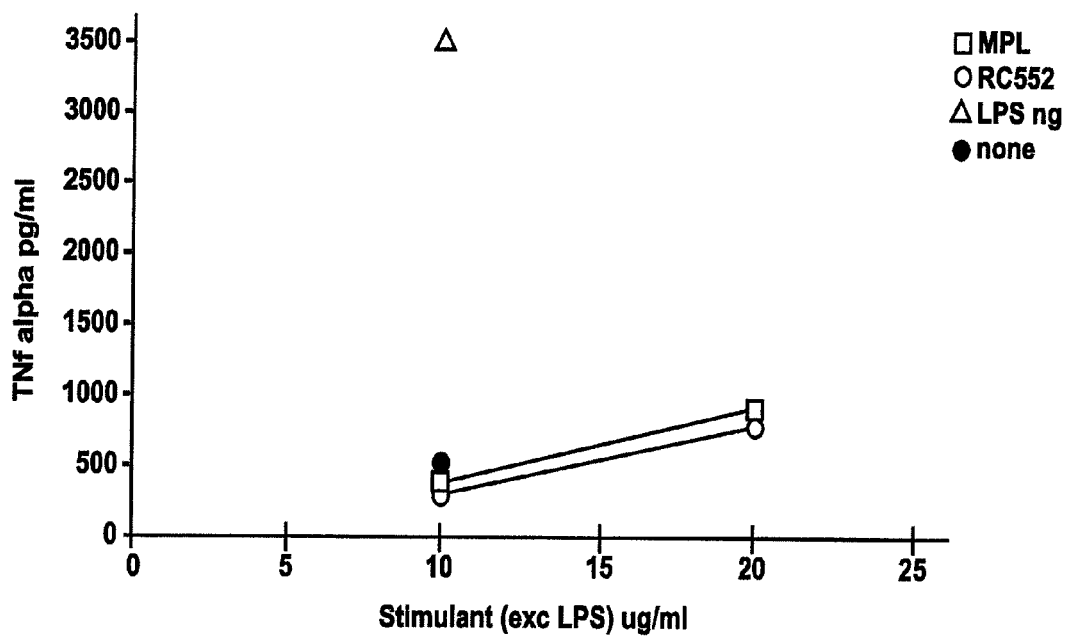
Figure 8A:
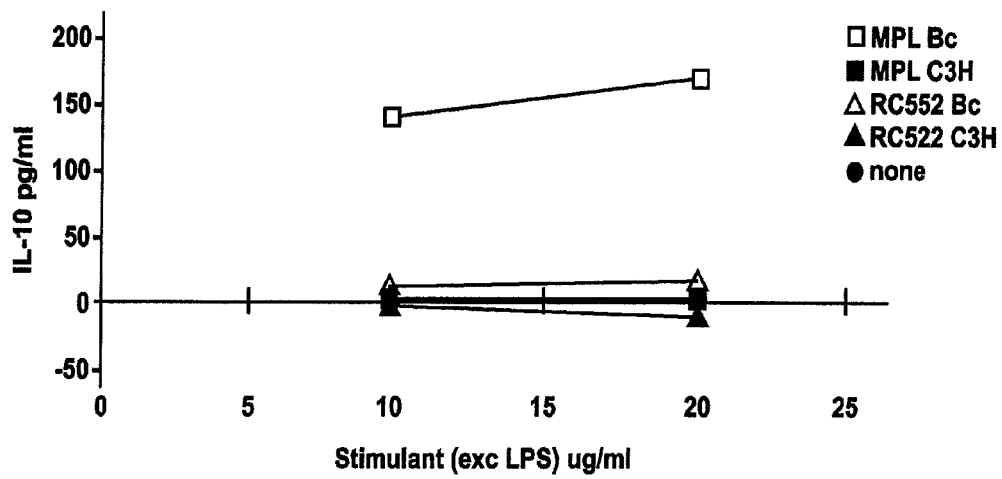
FIG. 8 are graphs depicting cytokine induction by RC522 as compared to MPL in murine (Balb/c and C3H/HEJ) splenic cultures.
Figure 8B:
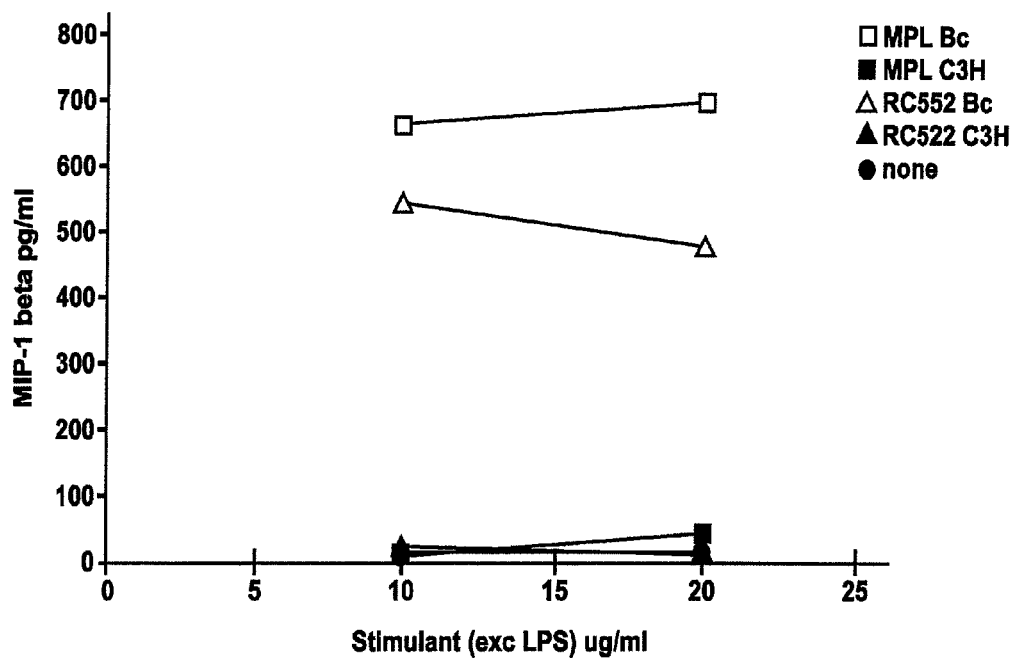
Figure 8C:
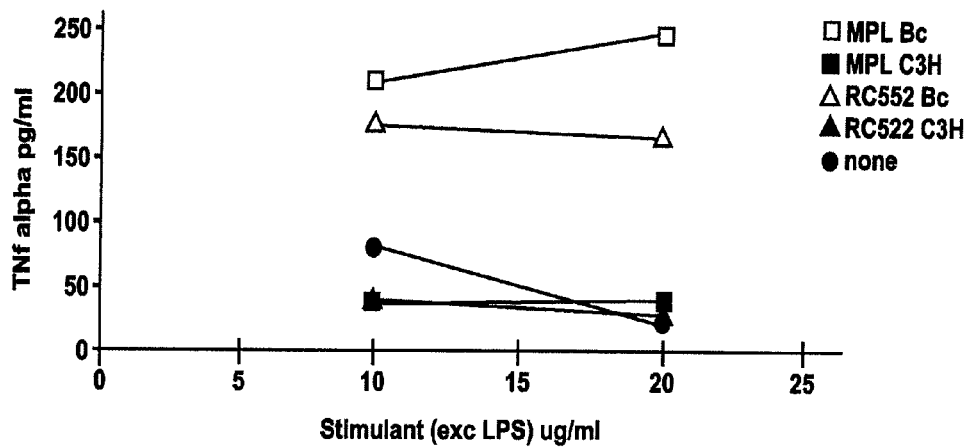
Figure 8D:
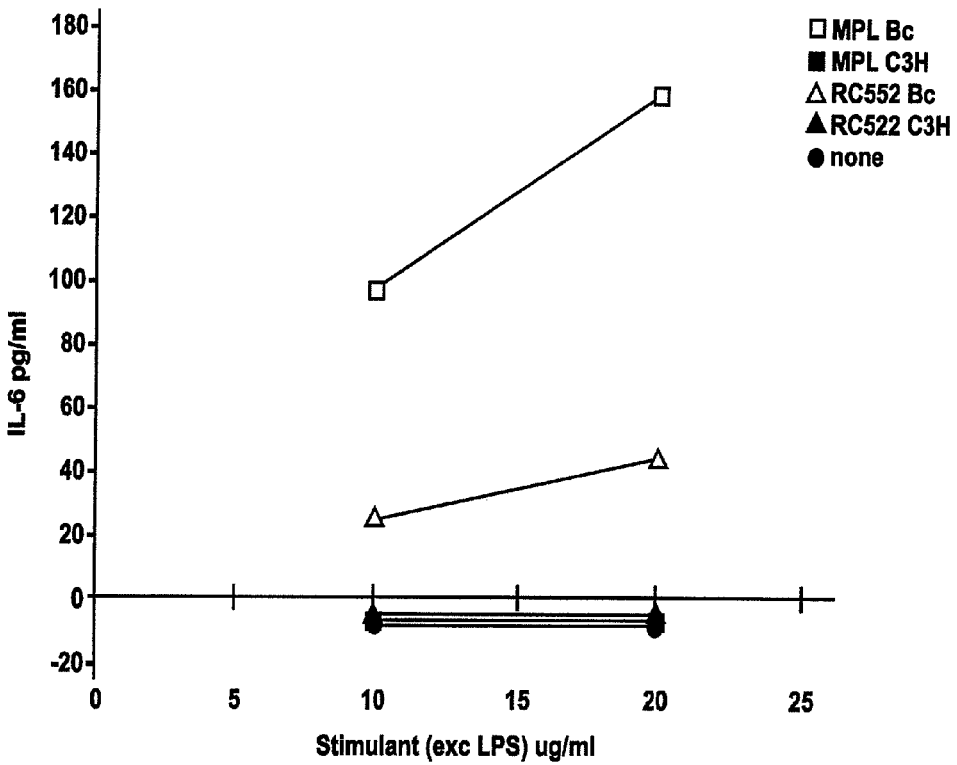
Figure 9A:
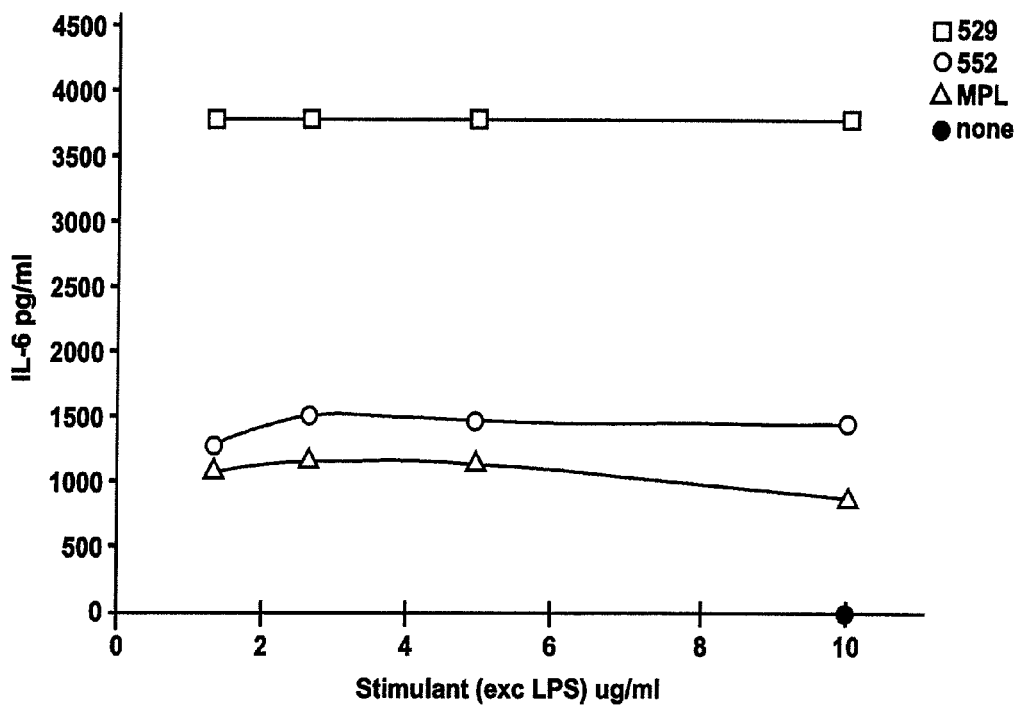
FIG. 9 are graphs depicting cytokine induction by RC529 and RC552 as compared to MPL in human peripheral blood mononuclear cells (PBMC).
Figure 9B:
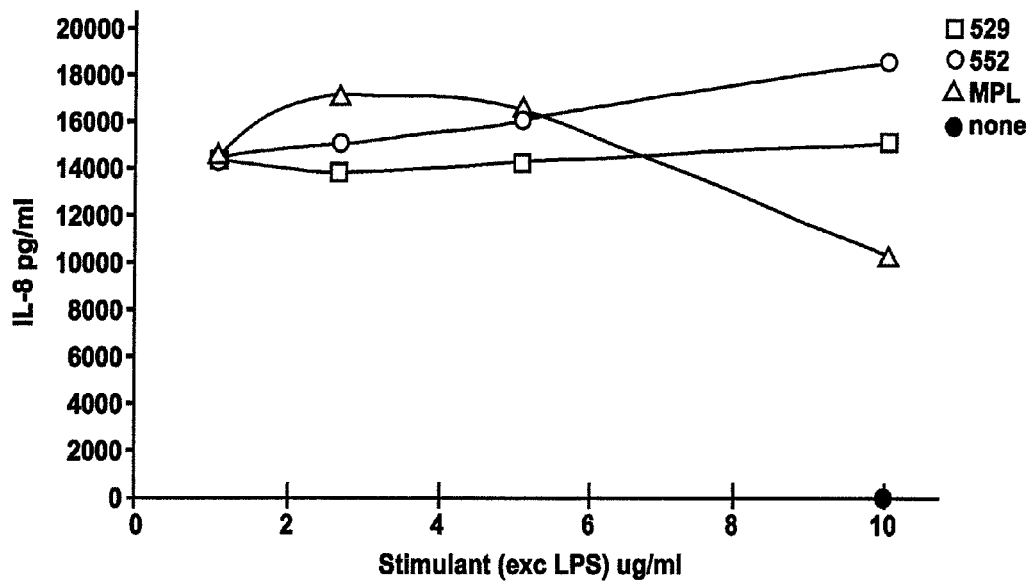
Figure 9C:
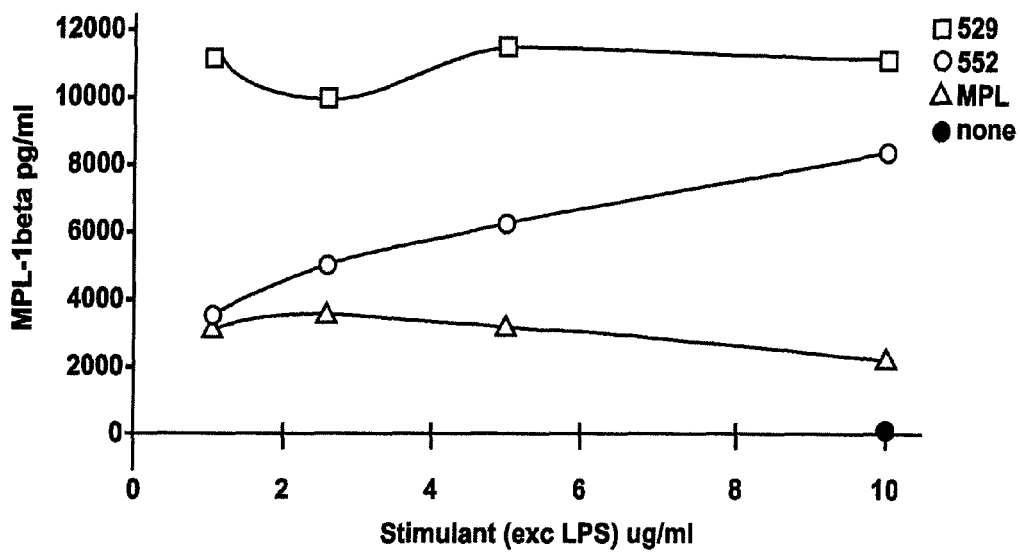
Figure 9D:
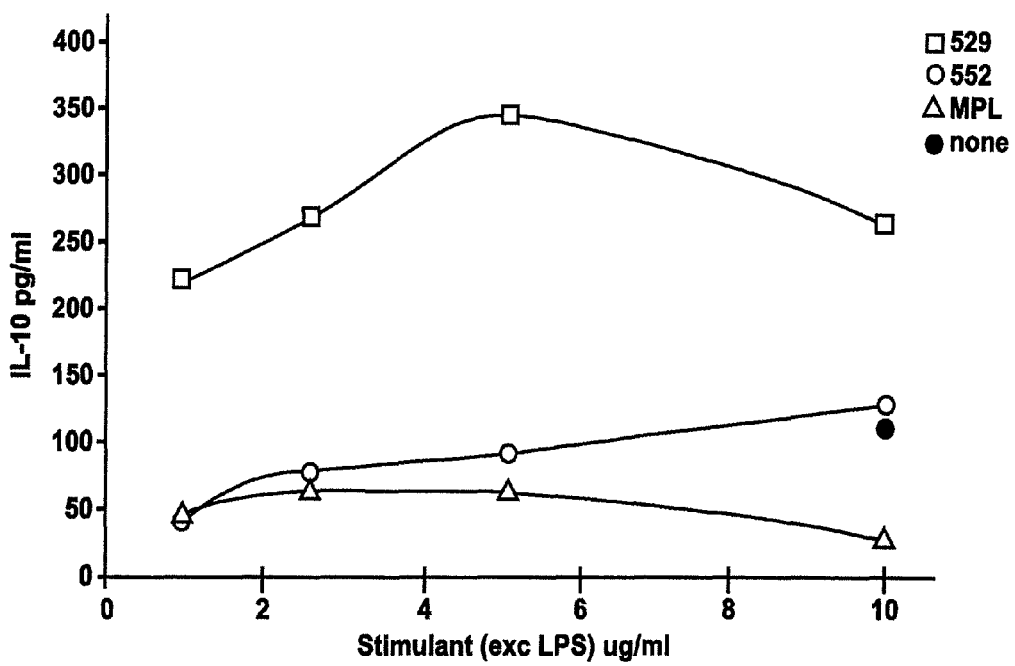
Figure 10A:
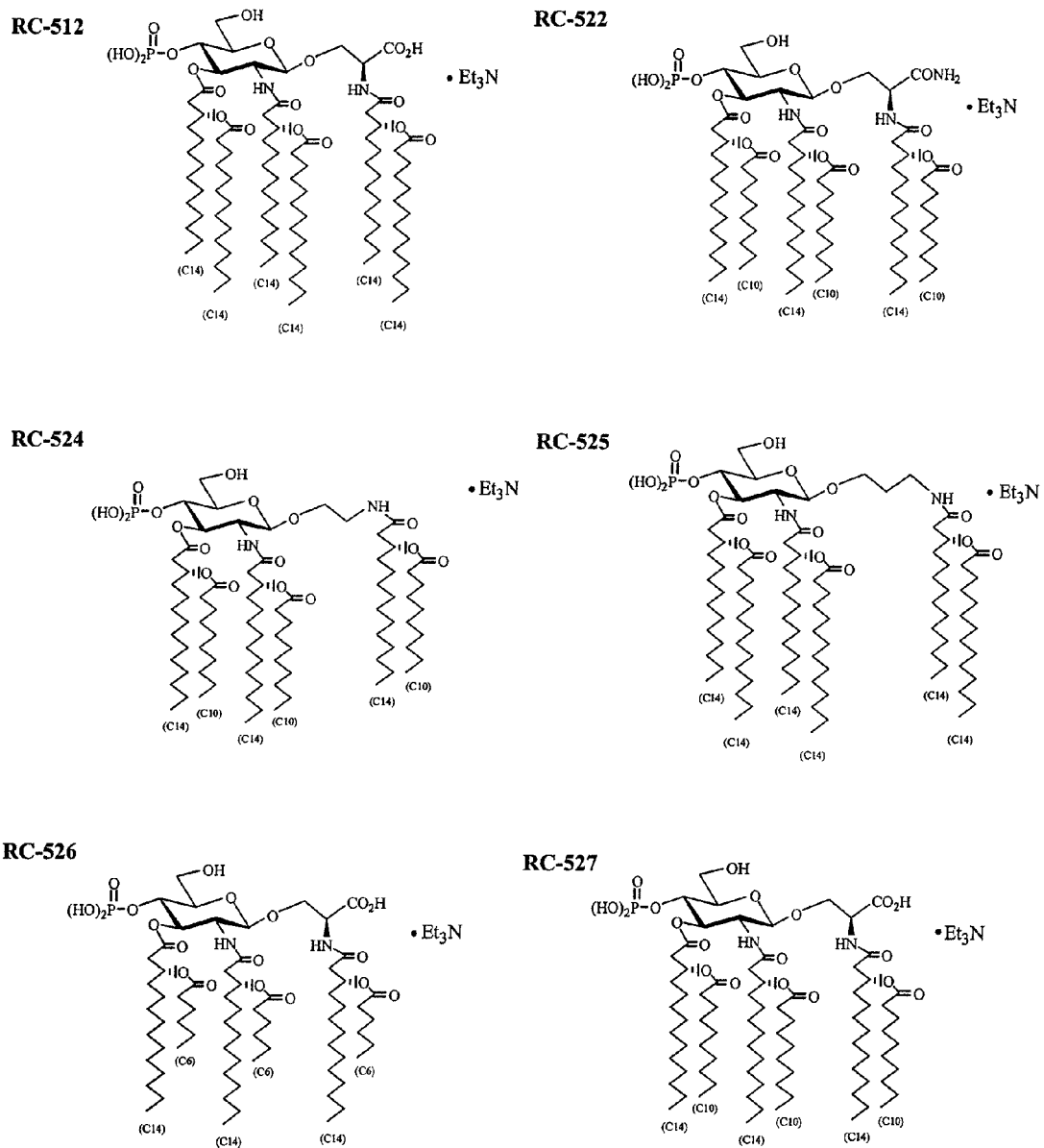
FIG. 10 A-E is a figure showing various AGP compounds.
Figure 10B:
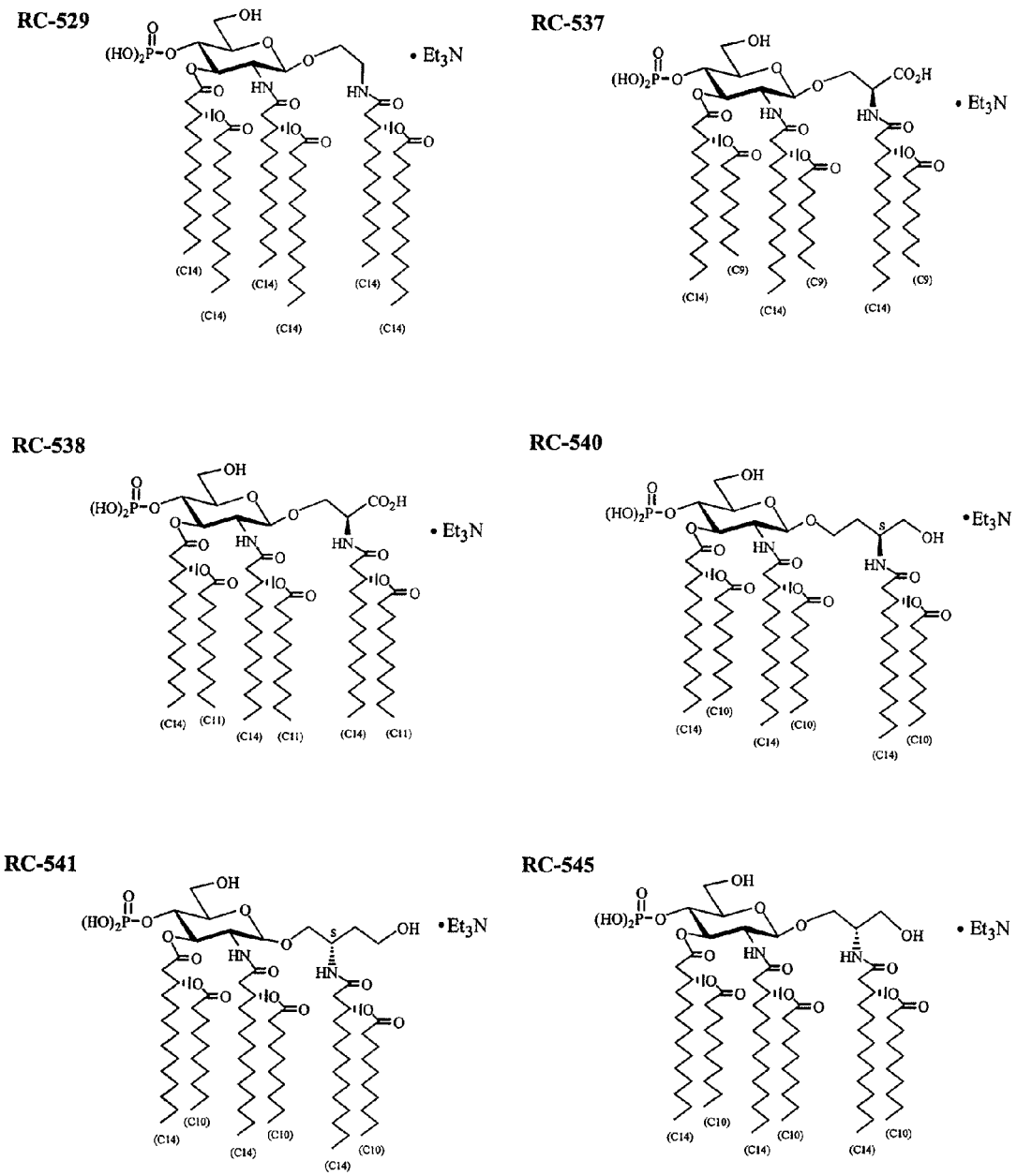
Figure 10C:
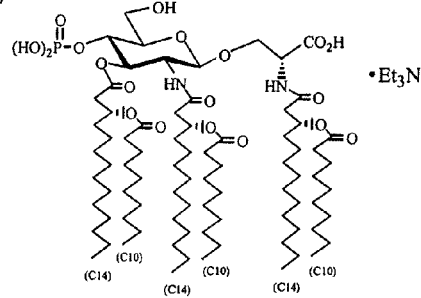
Figure 10C:
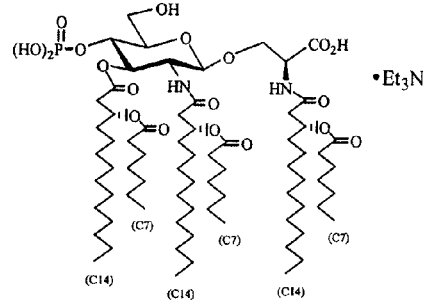
Figure 10C:
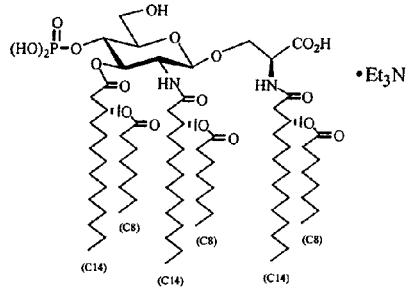
Figure 10C:
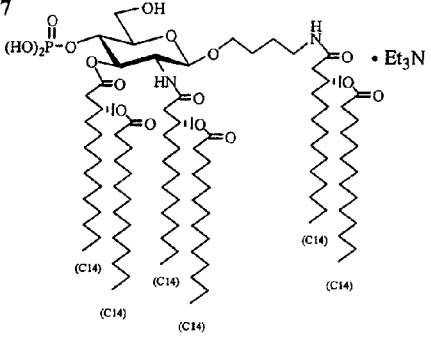
Figure 10C:
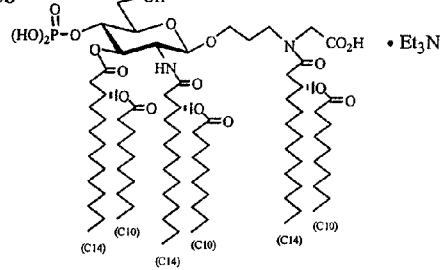
Figure 10C:
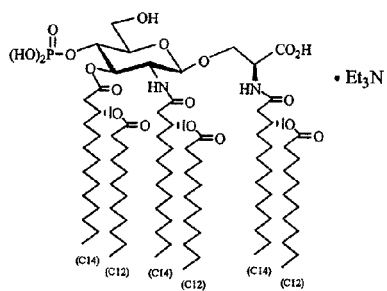
Figure 10D:
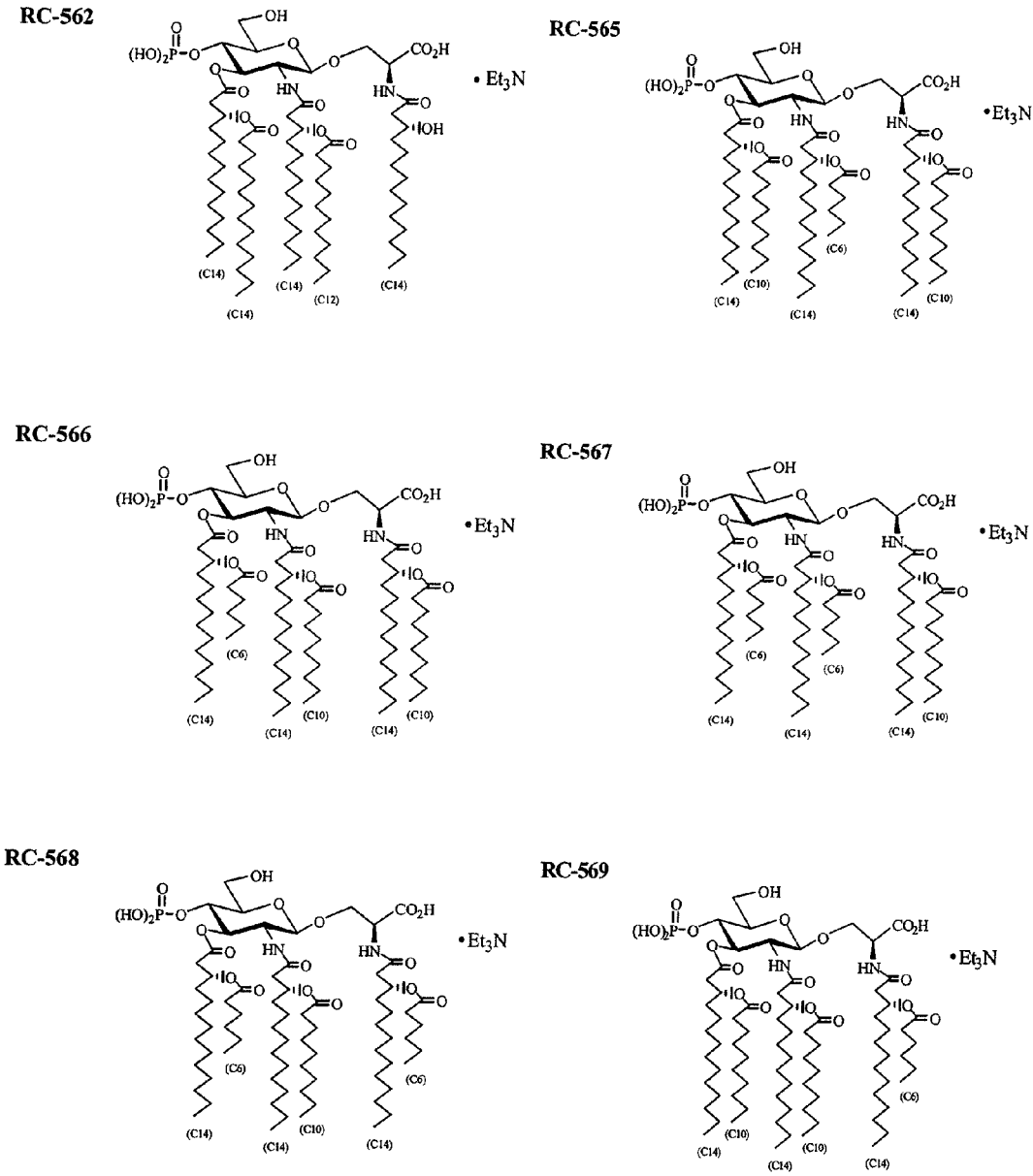
Figure 10E:
Figure 10E:
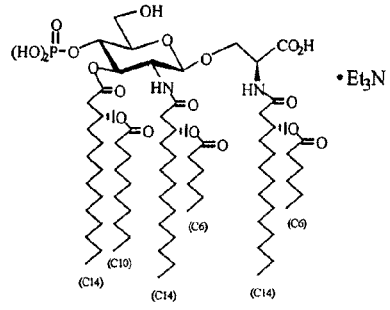
Figure 10E:
Figure 10E:
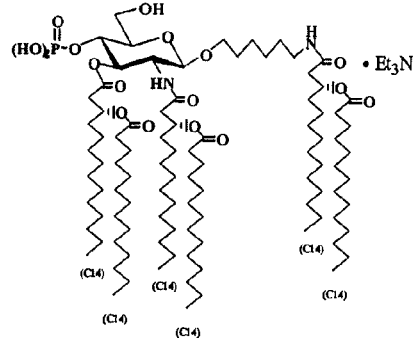
Figure 10E:
Figure 10E:
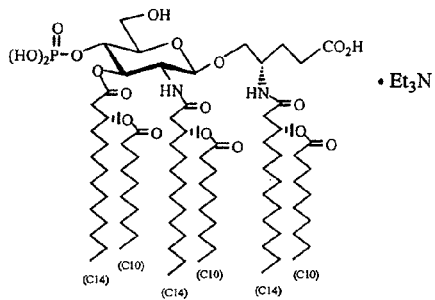

When tested in a solution of 0.2% triethanolamine, RC552 has a similar but not identical pro-inflammatory profile for TNF alpha induction as does MPL in two of three overnight cultures and one short-term culture of human whole blood. See, FIGS. 4-6 (overnight cultures for donors A-C, respectively) and FIG. 7 (short-term culture for donor A). In addition, MIP-1 beta induction by RC552 was similar in two of three overnight cultures. Lessened IL-10 was induced by RC552 than MPL in one overnight culture. IL-8 induction was different than that for MPL in all cases tested.

Using receptor deficient mice, it was clear that RC552 signals via toll-like receptor 4. Using BALB/c mice that are lipid A responsive, RC552 induced a lessened cytokine profile at the concentrations tested. Interestingly, the concentrations tested were at the high end of a dose response relationship, and RC552 induced slightly greater MIP-1 beta and TNF alpha at the lower concentration (10 □g/mL) than at the higher concentration (20 □g/mL) tested.

By comparing the human and mouse cytokine profiles, synthetic lipid A compound RC552 lessened capacity for IL-10 induction in 2 day mouse splenocyte cultures and in 1 of 3 human blood cultures overnight, when tested at high concentrations of stimulant. In general, less TNF alpha was induced in overnight human blood cultures by RC552 than MPL. About equal TNF alpha levels were induced in short term (5.5 hour) cultures of human blood by RC552 compared to MPL. Microarray data using RNA obtained from human macrophage stimulated with RC552 and MPL indicated early (1 hour) TNF alpha RNA for both compounds, and no late TNF alpha RNA for both compounds. RC552, however, induced very little 6 hour TNF alpha as opposed to MPL which had measurable 6 hour RNA.

In a separate set of experiments anticoagulated human whole blood was incubated in the presence of various AGPs and the supernatants were tested for quantities of cytokines. Into sterile 1.4 mL microtubes in a 96 well format (Matrix) were delivered 480 µL of human whole blood, and up to 20 µl of each AGP. Those AGPs tested included, L-Seryl AGP compounds varying in secondary fatty acid chain length (RC-526, RC-554, RC-555, RC-537, RC-527, RC-538, RC-560, RC-512) and L-Seryl AGPs having various combinations of 6 and 10 chain fatty acids (RC-570; RC-568, RC-567, RC-566, RC-565, RC-569, aminoethyl AGPs (RC-523, RC-524, RC-529, RC-577, see FIG. 10), L-serinamide AGPS (RC-522, and RC-515, see FIG. 10), and Serinol AGPs, (RC-545, RC-574, RC-519, RC-541, RC-540, and RC-517 see FIG. 10), and AGPs varying in backbone length, RC-529 (2 carbon linker), RC-525 (3 carbon linker), RC-557 (4 carbon linker), RC-571 (6 carbon linker).

The tubes were sealed with caps supplied by the manufacturer, and the 96 well plate apparatus was placed on its side so that the microtubes were horizontal, placed upon a "belly dancer" agitation platform, and cultured at 37° C. overnight, for 22 to 28 hours. At the conclusion of culture, the tubes with holder were centrifuged momentarily to remove blood from the caps of each tube, the tubes were opened and 500 µl of PBS were added, tubes sealed again, and inverted to mix. The addition of 500 µL of PBS facilitated centrifugation as well as recovery of plasma supernatants. Tubes in a plate holder were then centrifuged for 10 minutes at 1800 RPM in an IEC Centra 8R centrifuge. Two aliquots of 310 µL were then removed from each tube and stored frozen in a 96 well format until assayed for cytokine content. Cytokines (IFN, IL-2, IL-4, IL-5, IL-6, IL-8, MIP-1β, TNFα) were evaluated by ELISA (R and D Systems) and by cytometric bead array (BD Biosciences).

For each group of AGPs tested, two blood donors were used. Donor 1 and Donor 2 were not the same in all experiments reported in Tables 3 and 4. Each horizontal grouping represents one experiment in which donor 1 and donor 2 were the same for all tests within that group. As a positive control, separate samples of the same donor's blood were stimulated with purified phytohaemagluttinin (PHA, Sigma), LPS from *E coli* O55B5 (Sigma), *E. coli* DNA (Sigma) as well as MPL at doses up to 20 µl. Controls were used to determine the background state of the blood cells as well as the ability of the blood cells to be stimulated.

In general, results compare favorably with those found in influenza challenge model and the *Listeria* protection model, described herein. AGPs that were not active in these models did not induce cytokines in human blood cultures. AGPs that were weak protectors in mice, were weak inducers of cytokines in human whole blood cultures. AGPs that were very potent in mouse protection studies also were potent inducers of human cytokines. Table 3 summarized the results for cytokines IL-6, IL-8, MIP-1β, TNFα, IL-10 and IFNγ. The maximum level of cytokine obtained is reported. TNFα and IFNγ are induced early have peaked before the assay is performed at 24 hours. In addition, IFNγ has not been found in human blood cultures in a routine fashion, only sporadically. IFNγ induction was found in an isolated case of IFNγ/expression. Background IFNγ/levels for that donor were high (>200 pg/mL), suggesting that an immune response was in process.

Table 4 provides the maximum levels of IL-4, IL-2 and IL-5 obtained, as well as ratios of TNF to IL-10, and ratios of IL-10 to TNF. Inhibition data for IL-8, reported as a percentage, are also provided on the right hand side of Table 4. For example, 90% inhibition would calculate to a 90% reduction of cytokine levels. MIP-1β results were similar.

RC-526, RC-554, RC-555, RC-570, RC-568, RC-567, and RC-566 exhibited little if any cytokine stimulation but when added to Ogawa *P. gingivalis* LPS stimulated whole blood cells they inhibited LPS production of cytokines 90-100%. See Table 4. Such LPS blocking would be useful for applications where reduced LPS levels are desired. Topical application of such compounds would be useful to reduce bacteria levels prior to treatment, such as for dental surgery.

The results for RC-529 (2 carbon linker), RC-525 (3 carbon linker), RC-557 (4 carbon linker), RC-571 (6 carbon linker) suggest that as the aglycone carbon chain length increased, the cytokine stimulatory effect decreased, indicating that greatest stimulation was achieved when the fatty acid residues attached to the aglycone moiety were closely adjacent to the fatty acids attached to the glucosamine moiety.

TABLE 3

| AGP | IL-6 | | IL-8 | | MIP-1β | | TNFα cba | | IL-10 | | IFNγ cba | |
|---|---|---|---|---|---|---|---|---|---|---|---|---|
| RC# | donor 1 | donor 2 | donor 1 | donor 2 | donor 1 | donor 2 | donor 1 | donor 2 | donor 1 | donor 2 | donor 1 | donor 2 |
| 570 | − | − | − | − | − | − | | | + | − | − | |
| 568 | − | − | − | − | − | +/− | | | + | − | − | |
| 567 | − | − | − | − | − | +/− | | | + | − | − | |
| 566 | − | − | − | − | + | + | | | + | − | − | |
| 565 | − | − | + | ++ | ++ | ++ | | | +++ | +/− | − | |
| 569 | + | +/− | ++ | +++ | ++ | +++ | | | ++++ | + | − | |
| 539 | ++ | + | +++ | ++++ | +++ | +++ | | | ++++ | +++ | − | |
| 562 | +/− | − | + | +++ | ++ | ++ | | | ++++ | + | − | |
| MPL | + | +/− | +++ | ++++ | +++ | +++ | | | ++++ | + | − | |
| None | − | − | − | − | − | − | | | − | − | − | |
| LPS | + | + | ++ | +++ | +++ | ++++ | | | ++++ | +++ | − | |
| EcDNA | + | +/− | ++ | − | +++ | + | | | ++++ | − | − | |
| PHA | + | + | ++ | +++ | +++ | ++++ | | | ++++ | ++++ | + | |
| 526 | − | − | − | − | − | − | − | − | | | − | ++ |
| 554 | − | − | − | − | +/− | − | − | | | | − | ++ |
| 555 | − | + | +/− | +/− | +/− | − | − | | | | − | ++ |
| 537 | + | ++ | ++ | ++++ | ++++ | + | ++ | | | | − | ++ |
| 527 | + | ++ | + | ++++ | ++++ | +++ | +++ | | | | − | ++ |
| 538 | + | ++ | + | ++++ | ++++ | +++ | +++ | | | | − | ++ |
| 560 | + | ++ | + | ++++ | ++++ | ++ | +++ | | | | − | ++ |
| 512 | + | ++ | + | ++++ | +++ | − | ++ | | | | − | ++ |
| MPL | + | ++ | + | +++ | ++ | − | + | | | | − | + |
| None | − | − | − | − | − | − | − | | | | − | − |
| LPS | + | +++ | + | +++ | ++ | ++ | +++ | | | | − | ++ |
| EcDNA | + | +++ | + | +++ | +++ | +++ | +++ | | | | − | + |
| PHA | +/− | +/− | +/− | − | +/− | ++ | + | | | | +++ | ++ |
| 523 | + | − | +++ | − | + | + | − | − | − | − | +/− | − |
| 524 | ++ | + | ++++ | ++ | + | +++ | − | − | + | + | +/− | − |
| 529 | ++ | + | ++++ | ++ | + | ++ | − | − | + | + | +/− | − |
| 525 | ++ | + | ++++ | +++ | ++ | ++++ | + | + | + | + | +/− | − |
| 557 | ++ | + | ++++ | + | ++ | ++ | − | − | + | + | − | − |
| 571 | + | − | +++ | − | + | + | − | − | − | − | − | − |
| 577 | + | +/− | +++ | + | + | + | − | − | − | − | − | − |
| MPL | + | + | +++ | + | + | ++ | − | − | − | − | − | − |
| None | − | − | − | − | − | − | − | − | − | − | − | − |
| LPS | ++ | + | +++ | + | +++ | ++++ | + | + | + | ++ | +/− | + |
| EcDNA | ++ | ++ | + | ++ | +++ | ++++ | − | − | ++ | ++ | − | − |
| PHA | + | + | +++ | ++ | + | ++ | − | − | − | − | +/− | ++ |
| 522 | +++ | ++ | ++++ | +++ | +++ | +++ | + | + | | | − | − |
| 515 | +++ | +++ | ++++ | ++++ | +++ | ++ | + | − | | | − | − |
| 545 | ++ | + | ++++ | +++ | ++ | +++ | − | − | | | − | − |
| 544 | +++ | + | ++++ | +++ | +++ | ++ | ++ | − | | | − | − |
| 519 | ++ | + | ++++ | +++ | ++ | ++ | − | + | | | − | − |
| 541 | +++ | ++ | ++++ | ++ | ++ | ++ | − | − | | | − | − |
| 540 | ++ | ++ | ++++ | +++ | ++ | ++ | + | +/− | | | − | − |
| 517 | +++ | +++ | ++++ | ++++ | ++ | ++ | +/− | +/− | | | − | − |
| MPL | + | ++ | +++ | +++ | + | ++ | − | − | | | − | − |
| None | − | − | − | − | − | − | − | − | | | − | − |
| LPS | ++ | +++ | ++++ | ++++ | ++++ | +++ | ++++ | +/− | | | − | − |
| EcDNA | ++ | +++ | ++++ | ++++ | +++ | ++ | ++++ | + | | | − | − |
| PHA | +++ | +++ | ++++ | ++++ | ++++ | +++ | +++ | − | | | +++ | ++ |

TABLE 4

| AGP | | 10, 5, 2.5 ug/mL | | | | % inhib. | IL-1β cba2 | |
|---|---|---|---|---|---|---|---|---|
| | | | TNFα/IL10 cba | | IL10/TNFα cba | | | |
| RC# | IL-4 | IL-2 | IL-5 | donor 1 | donor 2 | donor 1 | donor 2 | LPS IL-8 | donor 1 | donor 2 |
| 570 | − | − | − | | | | | 100 | | |
| 568 | − | − | − | | | | | 96 | | |
| 567 | − | − | − | | | | | 100 | | |
| 566 | − | − | − | | | | | 93 | | |
| 565 | − | − | − | | | | | 16 | | |
| 569 | − | − | − | | | | | −13 | | |
| 539 | − | − | − | | | | | | | |
| 562 | − | − | − | | | | | | | |
| MPL | − | − | − | | | | | | | |
| None | − | − | − | | | | | | | |
| LPS | − | − | − | | | | | | | |
| EcDNA | − | + | − | | | | | | | |
| PHA | − | − | − | | | | | | | |
| 526 | − | − | − | 0.9 | | 1.2 | | 99 | 256 | |

TABLE 4-continued

| AGP RC# | IL-4 | IL-2 | IL-5 | 10, 5, 2.5 ug/mL TNFα/IL10 cba donor 1 | donor 2 | IL10/TNFα cba donor 1 | donor 2 | % inhib. LPS IL-8 | IL-1β cba2 donor 1 | donor 2 |
|---|---|---|---|---|---|---|---|---|---|---|
| 554 | − | − | − |  | 0.9 |  | 1.1 | 100 | 545 |  |
| 555 | − | − | − |  | 0.8 |  | 1.2 | 99 | 519 |  |
| 537 | − | − | − | 0.8 | 9.7 | 1.3 | 0.3 | 33 | 8353 |  |
| 527 | − | − | − | 2.5 | 3.4 | 0.4 | 0.3 | 5 | 7102 |  |
| 538 | − | − | − | 2.3 | 4 | 0.5 | 0.3 | −3 | 7767 |  |
| 560 | − | − | − | 0.8 | 5.1 | 1.3 | 0.2 | −1 | 5833 |  |
| 512 | − | − | − |  | 3.9 |  | 0.4 | −1 | 3230 |  |
| MPL | − | − | − |  | 1 |  | 1 |  | 1213 |  |
| None | − | − | − |  |  |  |  |  | 0 |  |
| LPS | − | − | − | 0.6 | 6.3 | 1.7 | 0.2 |  | 4414 |  |
| EcDNA | − | − | − |  | 8.7 |  | 0.1 |  | 9453 |  |
| PHA | − | ++ | − |  | 0.9 |  | 1.1 |  | 2023 |  |
| 523 | − | − | − |  |  |  |  | −47 |  |  |
| 524 | − | − | − | 0.2 | 0.3 | 1.8 | 4 | — |  |  |
| 529 | − | − | − | 0.4 |  | 6.2 |  | — |  |  |
| 525 | − | − | − | 1.8 | 1.2 | 3.7 | 0.7 | — |  |  |
| 557 | − | − | − | 0.6 | 0.5 | 0.6 |  | — |  |  |
| 571 | − | − | − | 0.5 |  | 8.6 |  | — |  |  |
| 577 | − | − | − |  |  |  |  | — |  |  |
| MPL | − | − | − |  |  |  |  |  |  |  |
| None | − | − | − | 0.3 |  |  |  |  |  |  |
| LPS | − | − | − | 0.1 |  | 3.2 | 2.5 |  |  |  |
| EcDNA | − | − | − |  | 0.4 | 8.3 | 3.3 |  |  |  |
| PHA | − | ++ | − |  |  |  |  |  |  |  |
| 522 | − | − | − | 0.4 |  | 2.7 |  |  |  |  |
| 515 | − | − | − | 0.4 | 0.8 | 3 | 1.4 |  |  |  |
| 545 | − | − | − |  |  |  |  |  |  |  |
| 544 | − | − | − | 0.6 |  | 1.7 |  |  |  |  |
| 519 | − | − | − |  |  |  |  |  |  |  |
| 541 | − | − | − |  |  |  |  |  |  |  |
| 540 | − | − | − | 0.2 | 0.2 | 5.5 | 5.2 |  |  |  |
| 517 | − | − | − | 0.3 | 0.7 | 3.9 | 1.4 |  |  |  |
| MPL | − | − | − |  |  |  |  |  |  |  |
| None | − | − | − |  |  |  |  |  |  |  |
| LPS | − | − | − | 1.7 | 0.3 | 0.7 | 4 |  |  |  |
| EcDNA | − | − | − | 1.8 | 0.5 | 0.6 | 2.7 |  |  |  |
| PHA | − | ++ | − |  |  |  |  |  |  |  |

Example 6

RC529 Stimulatory Capabilities Compared to MPL and RC552

This Example demonstrates that RC529 has superior immune stimulatory capabilities as compared to MPL when assessed by IL-6, IL-10 and MIP-1beta elaboration from human peripheral blood mononuclear cells (PBMC). In contrast, IL-8 elaboration was similar to that of MPL.

PBMC were stored frozen until used. PBMC donor designation was AD112. PBMC at a density of $6.26 \times 10^5$ were plated per well in a 48 well plate in 1.0 ml of medium. Medium consisted of RPMI-1640 plus sodium bicarbonate, 10% fetal bovine serum, 4 mM glutamine, 100 ug/ml gentamicin and 10 mM HEPES. PBMC were cultured for 22 hours at 37° C. in a carbon dioxide incubator. Supernatants were harvested and tested by ELISA (R&D Systems) for IL-6, IL-8, IL-10 and MIP-1 beta concentration. Cytokine concentration in supernatants was compared to supernatants obtained from unstimulated PBMC cultured identically.

At the doses tested, RC529 did not achieve dose-responsiveness at the lowest dose for IL-6 or IL-8. Compared to MPL, RC529 induced more IL-6, IL-10 and MIP-1 beta than did MPL. A disaccharide compound, RC552 was generally intermediate in stimulatory capability on a mass basis. See, FIG. 9. These data show that RC529 is a strong inducer of IL-6, IL-10 and MIP-1 beta from frozen human PBMC.

The same group of L-Seryl AGP compounds (RC-526, RC-554, RC-555, RC-537, RC-527, RC-538, RC-560, RC-512) and combined 6 and 10 chain fatty acids (RC-570, RC-568, RC-567, RC-566, RC-565, RC-569) as described above were tested and gave a result similar to that described using whole blood culture assay as described in Example 5. Those AGP compounds having secondary fatty acid chains of 9 carbons or more, or at least two 10 carbon fatty acids preferentially stimulated IL-6, IL-8, IL-10, and MIP-1β.

Example 7

Cell Surface Activation Markers

This experiment describes lineage specific cell surface activation markers in human PBMCs activated with LPS or selected AGPs. PBMCs were harvested from a normal donor and plated at $1 \times 10^7$ cells/well in a 16 wells (6 well plate) with 3 ml RPMI. LPS (10 ng/ml), RC-526 (10 μg/ml) or RC-527 (10 μg/ml) were added to each of 4 wells. Cells were harvested from each of 2 wells at 4 hr and 24 hr following activation and immediately stained for the lineage and cell surface activation markers.

Table 5 shows the percent expression of cell surface activation markers in the indicated cell lineage. Table 6 shows the mean fluorescent intensities of the indicated activation marker within each cell subset. This table only includes the cell surface activation markers that showed significant changes in the expression following a 4 hr or 24 hr incubation with LPS, RC-527 or RC-526.

TABLE 5

|  | No Activation | LPS | RC-527 | RC526 |
|---|---|---|---|---|
| 4 hr activation |  |  |  |  |
| T-cells (CD3+) |  |  |  |  |
| CD69+ | 1 | 5 | 10 | 1 |
| Mono/Macs (CD14+) |  |  |  |  |
| CD69+ | 2 | 19 | 22 | 1 |
| CD25+ | 1 | 1 | 1 | 1 |
| TLR2+ | 51 | 67 | 85 | 93 |
| B-cells (CD19+) |  |  |  |  |
| CD69+ | 4 | 39 | 56 | 11 |
| CD25+ | 0 | 0 | 0 | 0 |
| CD86+ | 3 | 4 | 8 | 4 |
| CD95+ | 6 | 6 | 7 | 6 |
| NK-Cells (CD56+) |  |  |  |  |
| CD69+ | 4 | 34 | 40 | 4 |
| CD3+ CD69+ | 2 | 11 | 11 | 1 |
| 24 hr activation |  |  |  |  |
| T-Cells (CD3+) |  |  |  |  |
| CD69+ | 3 | 8 | 10 | 2 |
| Mono/Macs (CD14+) |  |  |  |  |
| CD14+ CD69+ | 5 | 18 | 22 | 2 |
| CD14+ CD25+ | 1 | 90 | 70 | 1 |
| CD14+ TLR2+ | 18 | 80 | 97 | 79 |
| B-Cells (CD19+) |  |  |  |  |
| CD19+ CD69+ | 15 | 49 | 66 | 22 |
| CD19+ CD25+ | 5 | 35 | 34 | 9 |
| CD19+ CD86+ | 17 | 40 | 51 | 22 |
| CD19+ CD95+ | 14 | 71 | 73 | 15 |
| NK-Cells (CD56+) |  |  |  |  |
| CD69+ | 4 | 42 | 50 | 4 |
| CD3+ CD69+ | 2 | 11 | 16 | 2 |

TABLE 6

|  | % Expression | MFI | | | |
|---|---|---|---|---|---|
|  |  | No Activation | LPS | RC-527 | RC526 |
| 4 hr activation |  |  |  |  |  |
| Mono/Macs (CD14+) |  |  |  |  |  |
| CD11b+ | 100% | 2283 | 1650 | 1870 | 2154 |
| CD54+(ICAM-1) | 100% | 559 | 876 | 743 | 502 |
| B-cells (CD19+) |  |  |  |  |  |
| CD54+ (ICAM-1) | 100% | 57 | 57 | 65 | 55 |
| 24 hr activation |  |  |  |  |  |
| Mono/Macs (CD14+) |  |  |  |  |  |
| CD11b+ | 100% | 1737 | 893 | 1611 | 1986 |
| CD54+ (ICAM-1) | 100% | 1452 | 5290 | 4445 | 1590 |
| B-cells (CD19+) |  |  |  |  |  |
| CD54+ (ICAM-1 | 100% | 110 | 205 | 211 | 118 |

Note:
Cells from the 4 hr and 24 hr activation groups were stained and acquired on different days so the comparisons of MFI between time points is not suggested.

Example 9

Murine *Listeria monocytogenes* Challenge Model

This example provides experiments evaluating the induction of non-specific resistance in the murine *Listeria monocytogenes* challenge model performed using various AGPs and MPL. Mice (5 per group) were treated intravenously with the 1 µg of an AGP or MPL solubilized in 0.2% TEOA. Two days later the mice were challenged intravenously with a ~$10^5$ *L. monocytogenes* 10403 serotype (provided by M. L. Gray, Montana State University, Bozeman, Mont.). Two days after the challenge, the mice were sacrificed and the number of colony forming units (CFUs) in the spleens of individual mice were determined by plating 10-fold serial dilutions of splenic homogenates on tryptic soy agar plates. The degree of protection afforded by a given AGP or MPL was calculated by subtracting the average number of bacteria per spleen (log 10 value) in the group of mice treated with a given compound, from the average number of bacteria per spleen (log 10 value) in a control group that was "sham" treated with vehicle (0.2% TEOA) prior to challenge with *L. monocytogenes*.

Figure 14:
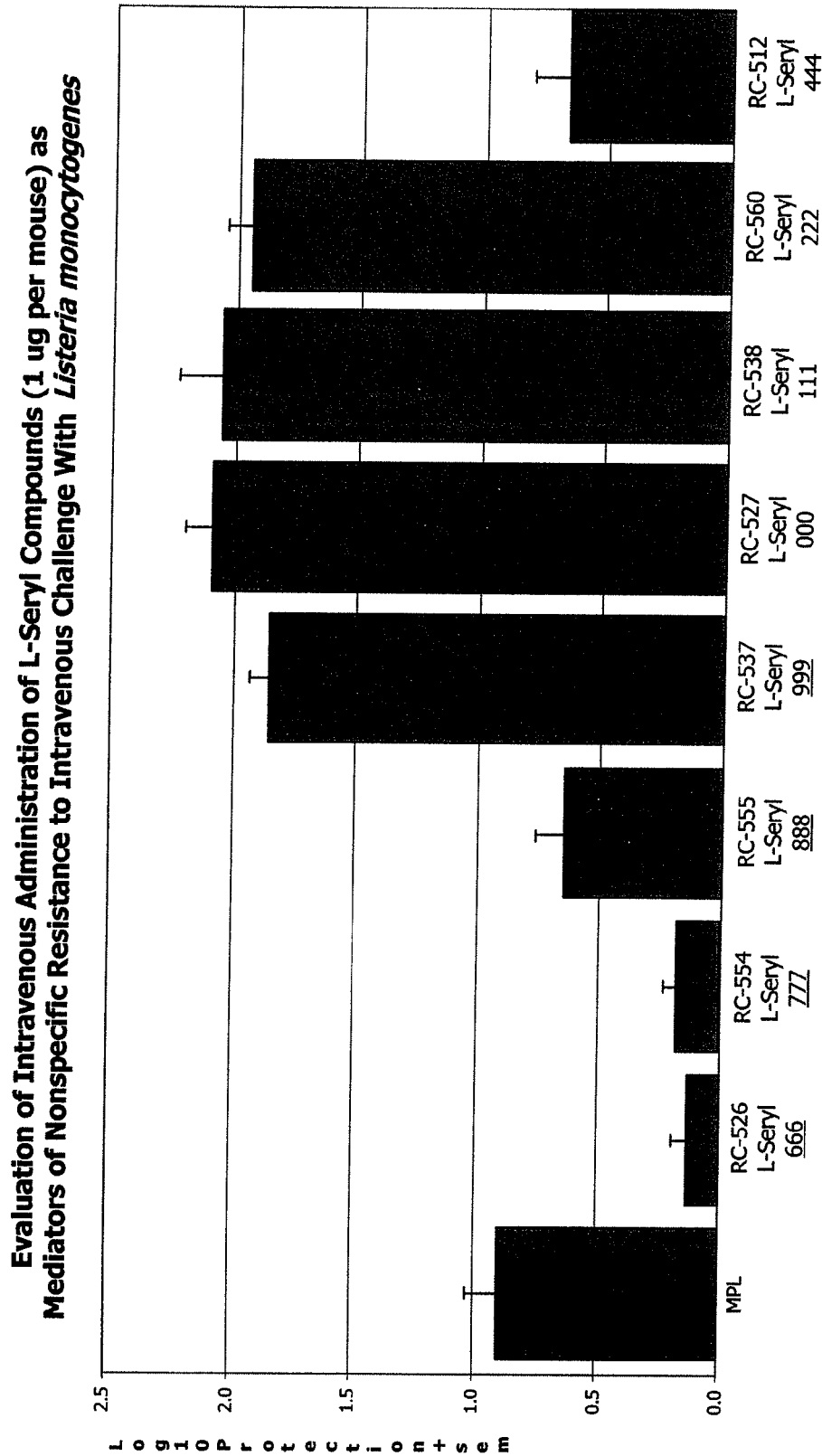
FIG. 14 is a graph showing clinical symptoms following intravenous administration of L-Seryl Aminoalkyl Glucosaminide Phosphates monotherapy and intravenous *Listeria monocytogenes* challenge.
Figure 15:
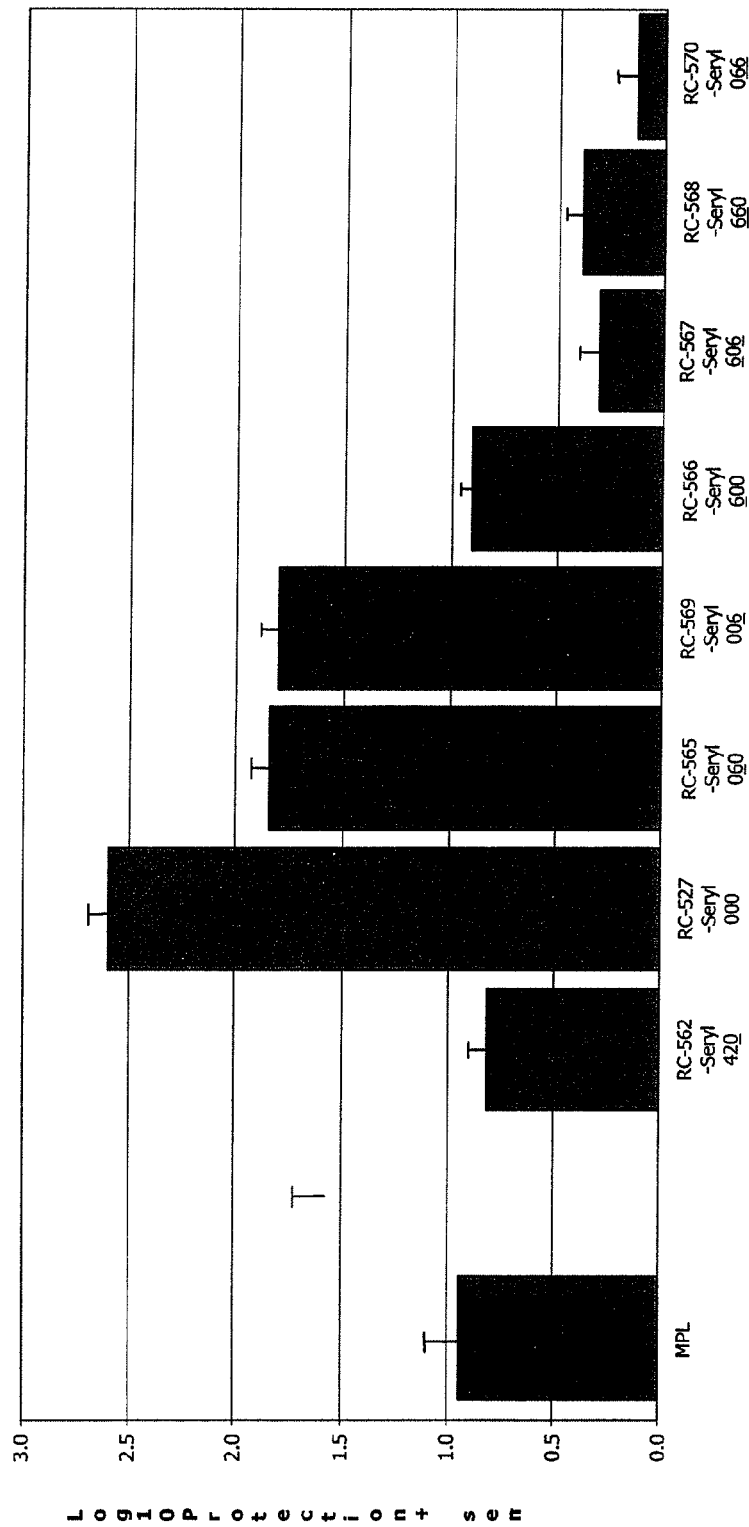
FIG. 15 is a graph showing clinical symptoms following intravenous administration of L-Seryl Aminoalkyl Glucosaminide Phosphates monotherapy and intravenous *Listeria monocytogenes* challenge. L-Seryl compounds have various combinations of 6 and 10 carbon fatty acid chains in the secondary fatty acid position.

The same group of L-Seryl AGP compounds (RC-526, RC-554, RC-555, RC-537, RC-527, RC-538, RC-560, RC-512) and combined 6 and 10 chain fatty acids (RC-570, RC-568, RC-567, RC-566, RC-565, RC-569), as described above, were tested. As was seen in the influenza model, those AGPs having fatty acids of 9 or more carbons in the secondary position provided the greatest protection, see FIG. 14. Those AGPs having at least two 10 carbon fatty acid chains in the secondary position were only slightly less protective than RC-527 which has three 10 carbon fatty acid chains, and were more protective than MPL, see FIG. 15.

Figure 16:
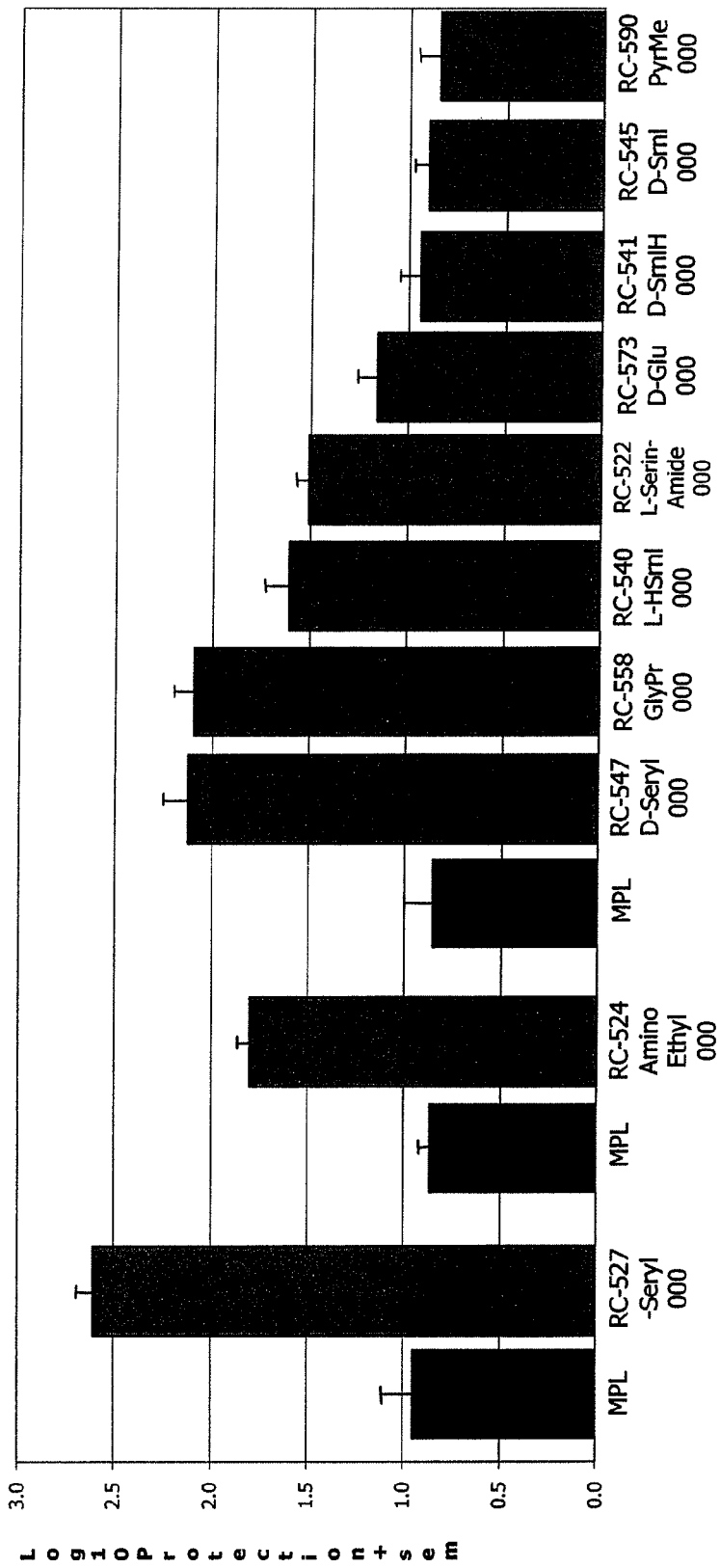
FIG. 16 is a graph showing clinical symptoms following intravenous administration of various Aminoalkyl Glucosaminide Phosphates monotherapy and intravenous *Listeria monocytogenes* challenge. The AGP compounds all have 10 carbon fatty acid chains in the secondary fatty acid position.

AGPs having 10-carbon fatty acids in the secondary position from various families were also tested. L-Seryl (RC-527), Pyrrolidinomethyl (RC-590), Aminoethyl (RC-524), Serinamides (RC-522), Serinols and Serinol regioisomers (RC-540, RC-541, and RC-545) and miscellaneous other (RC-547, RC-558 and RC-573) AGPs provided protection that was equal to or greater than that provided by MPL, see FIG. 16.

Figure 17:
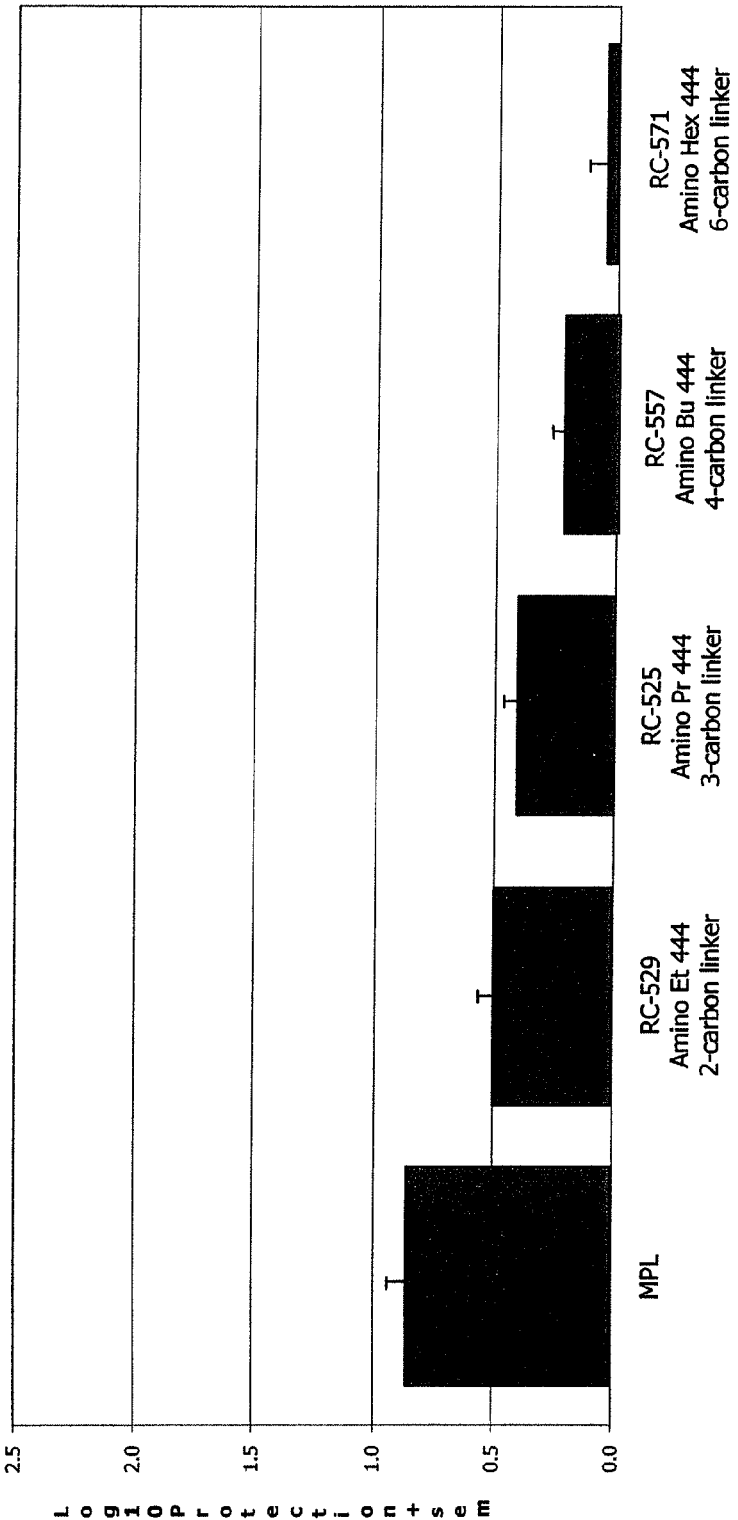
FIG. 17 is a graph showing clinical symptoms following intravenous administration of Aminoalkyl Glucosaminide Phosphates monotherapy and intravenous *Listeria monocytogenes* challenge. The AGP compounds vary in linker length between the glucosamine and aglycone moieties.

AGPs varying in linker length RC-529 (2 carbon linker), RC-525 (3 carbon linker), RC-557 (4 carbon linker), and RC-571 (6 carbon linker) again showed that the greatest protection was achieved when the fatty acid residues attached to the aglycone moiety were closely adjacent to the fatty acid residues attached to the glucosamine moiety, see FIG. 17.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:
1. A method of negatively modulating a Toll-like receptor in a subject in need thereof, the method comprising contacting the subject with an effective amount of one or more compounds having the formula:

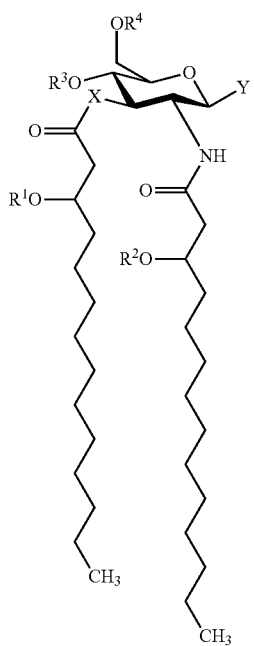

and pharmaceutically acceptable salts thereof, wherein
X is a member selected from the group consisting of —O— and —NH—;
$R^1$ and $R^2$ are each members independently selected from the group consisting of $(C_2-C_{24})$acyl;
$R^3$ is a member selected from the group consisting of —H and —PO$_3R^{11}R^{12}$, wherein $R^{11}$ and $R^{12}$ are each members independently selected from the group consisting of —H and $(C_1-C_4)$alkyl;
$R^4$ is a member selected from the group consisting of —H, —CH$_3$ and —PO$_3R^{13}R^{14}$, wherein $R^{13}$ and $R^{14}$ are each members independently selected from the group consisting of —H and $(C_1-C_4)$alkyl; and
Y is a radical having the formula:

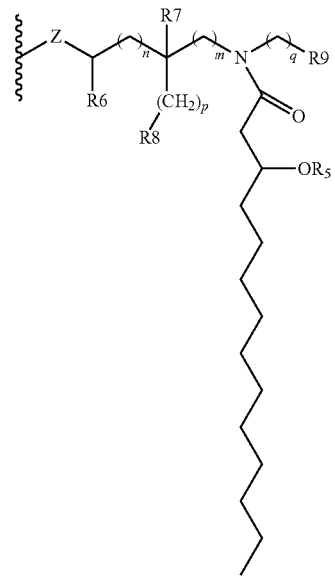

wherein the subscripts n, m, p and q are each independently an integer of from 0 to 6;
$R^5$ is $(C_2-C_{24})$acyl;
$R^6$ and $R^7$ are members independently selected from the group consisting of H and CH$_3$;
$R^8$ and $R^9$ are members independently selected from the group consisting of H, OH, $(C_1-C_4)$alkoxy, —PO$_3$H$_2$, —OPO$_3$H$_2$, —SO$_3$H, —OSO$_3$H, —NR$^{15}$R$^{16}$, —SR$^{15}$, —CN, —NO$_2$, —CHO, —CO$_2$R$^{15}$, —CONR$^{15}$R$^{16}$, —PO$_3$R$^{15}$R$^{16}$, —OPO$_3$R$^{15}$R$^{16}$, —SO$_3$R$^{15}$ and —OSO$_3$R$^{15}$ wherein R$^{15}$ and R$^{16}$ are each members independently selected from the group consisting of H and $(C_1-C_4)$alkyl; and
Z is —O— or —S—;
with the proviso that when $R^3$ is —PO$_3$R$^{11}$R$^{12}$, $R^4$ is other than —PO$_3$R$^{13}$R$^{14}$;
wherein at least two of said $R^1$, $R^2$ and $R^5$ are selected from the group consisting of $(C_2-C_6)$ acyl; and
wherein the one or more compounds is administered in the absence of exogenous antigen.

2. The method in accordance with claim 1, wherein the total number of carbon atoms in $R^1$, $R^2$ and $R^5$ is from about 6 to about 22.

3. The method in accordance with claim 2, wherein the total number of carbon atoms in $R^1$, $R^2$ and $R^5$ is from about 12 to about 18.

4. The method in accordance with claim 1, wherein $R^1$, $R^2$ and $R^5$ K are all $C_6$.

5. The method in accordance with claim 1, wherein X and Z are both —O—.

6. The method in accordance with claim 1, wherein m, n, p, and q are each independently an integer of from 0 to 2.

7. The method in accordance with claim 1, wherein $R^6$ and $R^7$ are H.

8. The method in accordance with claim 1 wherein the activity of the Toll-like receptor is associated with an autoimmune disease.

9. The method in accordance with claim 8, wherein said autoimmune disease is selected from the group consisting of inflammatory bowel disease, rheumatoid arthritis, chronic arthritis, multiple sclerosis and psoriasis.

10. The method in accordance with claim 9, wherein the autoimmune disease is inflammatory bowel disease.

11. The method in accordance with claim 1 wherein the activity of the Toll-like receptor is associated with an allergic condition.

12. The method in accordance with claim 11, wherein said allergic condition is selected from the group consisting of asthma, atopic dermatitis, seasonal allergic disorder and chronic rhinosinustis.

13. The method in accordance with claim 1, wherein said compound is administered to said subject by a route selected from the group consisting of parenteral, oral, intravenous, infusion, intranasal, inhalation, transdermal and transmucosal administration.

* * * * *